United States Patent [19]

Mac Leod

[11] Patent Number: 5,866,123
[45] Date of Patent: Feb. 2, 1999

[54] GENE ENCODING CATIONIC AMINO ACID TRANSPORTER PROTEIN

[75] Inventor: Carol L. Mac Leod, San Diego, Calif.

[73] Assignee: Research Development Foundation, Carson City, Nev.

[21] Appl. No.: 187,634

[22] Filed: Jan. 26, 1994

Related U.S. Application Data

[63] Continuation-in-part of Ser. No. 686,322, Apr. 11, 1991, Pat. No. 5,312,733, which is a continuation-in-part of Ser. No. 509,684, Apr. 13, 1990, abandoned.

[51] Int. Cl.[6] .......................... C07H 21/04; C07K 16/28; A61K 39/395; G01N 33/53
[52] U.S. Cl. ..................... 424/130.1; 424/143.1; 424/152.1; 530/387.1; 530/388.1; 530/388.22; 935/15
[58] Field of Search .................................. 435/69.1, 69.3, 435/69.6, 172.3, 240.27; 424/130.1, 184.1; 530/350, 387.1, 388.1; 935/15, 12

[56] References Cited

U.S. PATENT DOCUMENTS 5,171,850 12/1992 Filmus et al. .......................... 536/23.2

OTHER PUBLICATIONS

Closs et al., Journal of Biological Chemistry, vol. 268(10): 7538–7544, "Identification of a Low Affinity, High Capacity Transporter of Cationic Amino Acids in Mouse Liver" (Apr. 5, 1993).

Kim et al., Nature vol. 352:725–728, (1991).

*Primary Examiner*—Lila Feisee
*Assistant Examiner*—John Lucas
*Attorney, Agent, or Firm*—Benjamin Aaron Adler

[57] ABSTRACT

The present invention provides a novel gene encoding a cationic amino acid transporter protein. The present invention also provides antibodies specific for the cationic amino acid transporter protein. Further, the present invention provides methods of treating a disease characterized by undesirable levels of nitric oxide and methods of inhibiting cationic amino acid transport.

1 Claim, 31 Drawing Sheets gggtgtctttcctcatcgctgccctggcctcggttatggccggcctttgctatgctgaattt
agctgtgggccttcatcactggctggaatctcatcctgtcatatgtcataggtacgtccagt
ttttcaaaacgtacttcaaaatgaattacactggtctggcagagtatccagacttctttgcc
gggtgaataaattttttacagctattaatatcctggtccttctctttgtcATGGTGGCTGGGT
                                                       M  V  A  G
AGCAAGTGCTAGAGAACCACCTTCTGAGAACGGAACAAGCATCTACGGGGCTGGCGGCTTTA
  A  S  A  R  E  P  P  S  E  N  G  T  S  I  Y  G  A  G  G  F̲
GGGCTTTGACTGCATTGCAACAACCGGTGAAGAGGTTCGGAATCCACAAAAGGCGATCCCCA
  G  F  D  C  I  A  T  T  G  E  E  V  R  N  P  Q  K  A  I  P̲
TTTAACGCTTATGATGCCTTACTACCTCCTGGATGAGAAAAGTCCACTCCCAGTCGCGTTTG
  L  T  L  M  M  P  Y  Y  L  L  D  E  K  S  P  L  P  V  A  F
ATCAACAAGTCTTCTTGGATCCATTTTCCCAATGCCTCGTGTAATCTATGCTATGGCGGAGG
  S  T  S  L  L  G  S  I  F  P  M  P  R  V  I  Y  A  M  A  E
TGCTACTTTGTCATCGGGTGCAGTGGCAGCTGTGATGGCCTTTCTTTTTGACCTGAAGGCCC
  A̲  T̲  L̲  S̲  S̲  G̲  A̲  V̲  A̲  A̲  V̲  M̲  A̲  F̲  L̲  F̲  D̲  L̲  K  A
GCTTATTCTCAGGTACCAACCTGGCTTGTGTTACGAGCAGCCCAAATACACCCCTGAGAAAG
  L̲  I̲  L  R  Y  Q  P  G  L  C  Y  E  Q  P  K  Y  T  P  E  K
GCAAGGACAGGGTTTCAGCCTACGAACCCTCTTCAGCCCCTCTGCCCTGCCCACACGACAGT

FIGURE 3A

```
ggggcccgagtacccaagactggatctgcgtatctatacacttacgtcacggtcggag  120
gtcgcaagagcatggagtggcacctttgacgaacttcttaataaacagattggccagt  240
gtgtgccttgtattactcctggcaggtcttttatcttttggagtaaaagagtctgctt  360
TTGTGAAAGGAAATGTGGCTAACTGGAAGATCAGTGAAGAGTTTCTCAAAAATATATC  480
 F  V  K  G  N  V  A  N  W  K  I  S  E  E  F  L  K  N  I  S
TGCCCTATGGCTTTACAGGGACGTTGGCTGGTGCTGCAACGTGCTTTTATGCCTTTGT  600
 M  P  Y  G  F  T  G  T  L  A  G  A  A  T  C  F  Y  A  F  V
TCGGAATAGTGACGTCCTTACTTGTCTGCTTTATGGCTTACTTTGGGGTTTCTGCAGC  720
 I  G  I  V  T  S  L  L  V  C  F  M  A  Y  F  G  V  S  A  A
AGTATGTCAGATGGGGCCCCGCCAAATACGTTGTCGCAGCAGGCTCCCTCTGCGCCTT  840
 E  Y  V  R  W  G  P  A  K  Y  V  V  A  A  G  S  L  C  A  L
ATGGGTTGCTTTTCAAATGTCTAGCTCAAATCAATTCCAAAACGAAGACACCAGTAAT  960
 M  G  L  L  F  K  C  L  A  Q  I  N  S  K  T  K  T  P  V  I
TCGTGGACATGATGTCTATTGGCACCCTCATGGCCTACTCTCTGGTGGCAGCCTGTGT 1080
 L  V  D  M  M  S  I  G  T  L  M  A  Y  S  L  V  A  A  C  V
AAACTCTGGAATCATGTACCAATGCGACTTTGAAGAGCGAGTCCCAGGTCACCATGCT 1200
 E  T  L  E  S  C  T  N  A  T  L  K  S  E  S  Q  N  T  M  L
CGGCTTCCCTTGTGAGCTTTCTGGTGGGATTCCTGGCTTTCCTCATCCTGGGCTTGAG 1320
```

FIGURE 3B

```
  Q   G   Q   G   F   S   L   R   T   L   F   S   P   S   A   L   P   T   R   Q
TATTCTAACCACGTATGGCGTCCAGGCCATTGCCAGACTGGAAGCCTGGAGCCTGGCTCTTC
  I   L   T   T   Y   G   V   Q   A   I   A   R   L   E   A   W   S   L   A   L
GAATCAGCAAAAAGTAGCCTTCATGGTCCCGTTCTTACCGTTTCTGCCGGCCTTCAGCATCC
  N   Q   Q   K   V   A   F   M   V   P   F   L   P   F   L   P   A   F   S   I
CTGGATGGCGCTTGGCTTTCTGATCTATTTCGCCTATGGCATTAGACACAGCTTGGAGGGTA
  W   M   A   L   G   F   L   I   Y   F   A   Y   G   I   R   H   S   L   E   G
AGAAGAAAAGTCCGTCATGCAAGCAAATGACCATCACCAAAGAAACCTCAGCTTACCTTTCA
  E   E   K   S   V   M   Q   A   N   D   H   H   Q   R   N   L   S   L   P   F
ttaacaatgagtacactgtggccggatgccaccatcgtgctgggctgtcgtgggtctgctgt
attctgtgtctgaggagactgcctgagagcactcctcagctatatgtatccccaaaacagta
tctgtgacataattccagcatggtaattggtggcatatactgcacacactagtaaacagtat
tttctttattaggtatatgaccatcagtttggacatactgaaatgccatccctgtcaggat
aatgcatatatccttctcctacttgctaagacagctttcttaaacggccagggagagtgttt
```

FIGURE 3C

```
S  A  S  L  V  S  F  L  V  G  F  L  A  F  L  I  L  G  L  S
TCGCCCTGTTCCTTGTCCTCTGCGCTGCCGTCATTCTGACCATTTGGAGGCAGCCACA   1440
   L  A  L  F  L  V  L  C  A  A  V  I  L  T  I  W  R  Q  P  Q
TGGTCAACATTTACTTGATGGTCCAGTTAAGTGCGGACACTTGGATCAGATTCAGCAT   1560
   L  V  N  I  Y  L  M  V  Q  L  S  A  D  T  W  I  R  F  S  I
ACCCCAGGGACGAAGAAGACGATGAGGATGCCTTTTCAGAAAACATCAATGTAGCAAC   1680
   N  P  R  D  E  E  D  D  E  D  A  F  S  E  N  I  N  V  A  T
TACTTCATGAAAAGACAAGTGAATGttgatgctggccctcggtcttaccacgcatacc   1800
   I  L  H  E  K  T  S  E  C
ggacatggcttgcctaacttgtacttcctcctccagacagcttctcttcagatggtgg   1920
tgtccgtgtgcgtacatgtatgtctgcgatgtgagtgttcaatgttgtccgttattag   2040
attgctgaatagagatgtattctgtatatgtcctaggtggctggggaaatagtggtgg   2160
gtttaacagtggtcatgggtggggaagggataaggaatgggcattgtctataaattgt   2280
ctttcctctgtatgacaagatgaagaggtagtctgtggctggagatggccaatcc     2397
```

FIGURE 3D

```
  1  GGGTGTCTTTCCTCATCGCTGCCCTGGCCTCGGTTATGGCCGGCCTTTGCTATGCTG
      |  ||  ||| ||  ||||| ||  |||||  |  ||||||||||| |||||  | |
400  ATCTCCTTCTTGATTGCTGCTCTCGCCTCCGTGCTGGCCGGCCTGTGCTACGGCG

121  AGCTGTGGGCCTTCATCACTGGCTGGAATCTCATCCTGTCATATGTCATAGGTACGT
     ||||  |||||||||||||||||||||||  ||| || ||  || ||  |||| ||  |
518  AGCTTTGGGCCTTCATCACTGGCTGGAACCTGATTCTCTCCTACATCATCGGTACTT

241  TTTTCAAAACGTACTTCAAAATGAAT   TACACTGGT CTGGCAGAGTATCCAGACT
     | |      | |||  |      |||||   |  |   ||| |||||  |     ||  || |||
638  TCTCACGTCAGCACATGGCCCTGAATGCTCCTGGGGTGCTGGCCCAAACCCCGGACA

358  CTTGGGTGAA TAAATTTTTACAGCTATTAATATCCTGGTCCTTCTCTTTGTCATGG
     |    ||| ||  ||||||||  ||    ||| |||||||||| ||   ||| || ||| |||
758  CCATGGTCAACAAAATTTTCACCTGTATCAATGTCCTGGTCTTGTGCTTCATCGTGG

477  TATCAGCAAGTGCTAGAGAACCACCTTCTGAGAACGGAACAAGCATCTACGGGGCTG
     | ||  |    || ||  | ||  ||  |   |  |  ||||  | ||        ||||| |   |
869  TCTC  C   TG TA ACAA CAACGACACA AACGTGA AA         TACGGTGAGG

597  TTGTGGGCTTTGACTGCATTGCAACAACCGGTGAAGAGGTTCGGAATCCACAAAAGG
     | |||||||||||||||||||||| || || || || |||||  ||   |||  || || |||
974  TCGTGGGCTTTGACTGCATCGCCACCACAGGGGAAGAAGTCAAGAACCCCCAGAAGG

717  CAGCTTTAACGCTTATGATGCCTTACTACCTCCTGGATGAGAAAAGTCCACTCCCAG
     |  |||  |  ||||||  |||||||||  ||  |  |  ||||||  |  || ||  || ||  |
109  CCGCTCTCACGCTCATGATGCCTTACTTCTGCCTGGACATCGACAGCCCGCTGCCTG

837  CCTTATCAACAAGTCTTCTTGGATCCATTTTCCCAATGCCTCGTGTAATCTATGCTA
     |  |  |   ||   |||  || || ||||| || || |||||  || || ||||||||| |
1214 CACTTTCCACCAGTCTCCTAGGCTCCATGTTTCCCATGCCCCGAGTTATCTATGCCA

957  TAATTGCTACTTTGTCATCGGGTGCAGTGGCAGCTGTGATGGCCTTTCTTTTTGACC
     |||| ||  |||  ||  |  |  ||  ||  |    || |||||||||||||||| ||  |||| |
1334 TAATCGCCACTGTGACCTCAGGCGCCATTGCTGCTGTGATGGCCTTCCTCTTTGAAC

1077 GTGTGCTTATTCTCAGGTAC        CAACCTGGCTTGTGTTACGAGCAGCCCA
     ||||  |   |   |  |||||              ||||||    ||    ||| ||    | |||
1454 GTGTTTTGGTCTTACGGTACCAGCCAGAACAACCTAATCTGGTATACCAGATGGCCA
```

FIGURE 11A

```
AATTTGGGGCCCGAGTACCCAAGACTGGATCTGCGTATCTATACAGTTACGTCACGGTCGGAG
 | |||||  |||||  ||  |||||||| || || || ||  ||  ||||  |||||  |||||  ||  |
AGTTTGGTGCCCCTGTCCCCAAGACGGGCTCAGCCTACCTCTACAGCTACGTGACGGTGGGGG

CCAGTGTCGCAAGAGCATGGAGTGGCACCTTTGACGAACTTCTTAATAAACAGATTGGCCAGT
| || || ||||||||| |||||||  || |||||||| ||  |      || |  || ||   |||
CAAGCGTGGCAAGAGCCTGGAGTGCGACTTTTGACGAGCTGATAGGCAAGCCCATCGGAGAGT

TCTTTGCCGTGTGCCTTGTATTACTCCTGGCAGGTCTTTTATCTTTTGGAGTAAAAGAGTCTG
| ||||| |||     |  |  |  ||  |  ||||  ||  |||  ||  ||||  ||  ||||| |
TATTTGCTGTGATTATAATTATCATCTTAACAGGACTGTTAACTCTTGGCGTGAAGGAGTCAG

TGGCTGGGTTTGTGAAAGGAAATGTGGCTAACTGGAAGATCAGTGAAGAGTTTCTCAAAAATA
|||| ||||||  |||||||||     |       ||||||| || |||   |||        ||||||
TGTCCGGGTTCGTGAAAGGCTCCATTAAAAACTGGCAGCTCA CG   GAG        AAAAATT

GCGCCTTTATGCCCTATGGCTTTACAGGGACGTTGGCTGGTGCTGCAACGTGCTTTTATGCCT
|  ||  |||||||||| |||   |   | |      ||  || || || ||  || ||||||||||||
GAGGGTTTATGCCCTTTGGATTCTCTGGTGTCCTGTCAGGGGCAGCGACCTGCTTTTATGCCT

CGATCCCCATCGGAATAGTGACGTCCTTACTTGTCTGCTTTATGGCTTACTTTGGGGTTTCTG
| ||| ||  || ||  || ||| ||||| | ||||||||  || ||||||||| || |||  || || |
CCATTCCTGTGGGCATCGTGGCGTCCCTCCTCATTTGCTTCATAGCGTACTTTGGCGTGTCCG

TCGCGTTTGAGTATGTCAGATGGGGCCCCGCCAAATACGTTGTCGCAGCAGGCTCCCTCTGCG
 || ||  || |    | ||||    || || ||||  || ||   ||  |||| |||||||||
GTGCCTTCAAGCACCAGGGCTGGGAAGAAGCTAAGTACGCAGTGGCCATTGGCTCTCTCTGCG

TGGCGGAGGATGGGTTGCTTTTCAAATGTCTAGCTCAAATCAATTCCAAAACGAAGACACCAG
||||  || |||||   |  ||  || ||  ||||    |  ||  ||||||| |  || || ||||||| |
TGGCTGAAGATGGACTACTGTTTAAATTTTTGGCCAAAATCAACAATAGGACCAAAACACCCG

TGAAGGCCCTCGTGGACATGATGTCTATTGGCACCCTCATGGCCTACTCTCTGGTGGCAGCCT
|||||| ||| |||||| | ||||| |||||||| |||| |||| |||||||| |||||| ||||
TGAAGGACCTGGTGGACCTCATGTCCATTGGCACTCTCCTGGCTTACTCTTTGGTGGCTGCCT

AATACACCCCTGAGAAAGAAACTCTGGAATCATGTACCAATGCGACTTTGAAGAGCGAGTCCC
| |||||   |||   ||| |  |  ||||  |  |   |   |  ||  ||  ||  ||  || || || |
GAACCACCGAGGAGCTAGATCGAGTAG ATCA GAATGAGCTGGTCAGTG CCAGTGAATCAC
```

FIGURE 11B

```
1188 AG   GTCACCATGCTGCAAGGACAGGGTTTCAGCCTACGAACCCTCTTCAGCCCCT
     ||   | |    |  | | ||  ||   ||     ||  | || || ||    |||
1571 AGACAGGCTTTTTACCGGTAGCCGAGAAGTTTTCTCTGAAATCCATCCTCTCACCCA

1302 TCCTCATCCTGGGCTTGAGTATTCTAACCACGTATGGCGTCCAGGCCATTGCCAGAC
     || |||  |  |     ||| |  ||| |  |  ||  |||  ||||| | |||  |
1691 CTCTTATCATCACCGTGTGCATTGTGGCCGTGCTTGGAAGAGAGGCCCTGGCCGAAG

1422 CCATTTGGAGGCAGCCACAGAATCAGCAAAAAGTAGCCTTCATGGTCCCGTTCTTAC
     |||  ||||| |||||  |||  ||   |  |   ||| |||  || || |   | |
1811 TCATCTGGAGACAGCCTGAGAGCAAGACCAAGCTCTCATTTAAGGTACCCTTTGTCC

1542 CTTGGATCAGATTCAGCATCTGGATGGCGCTTGGCTTTCTGATCTATTTCGCCTATG
     | ||| || ||    | |||||| | | | ||  || |||||||||||||||  |||
1931 CGTGGGTCCGGTTTGCAGTGTGGATGCTGATAGGTTTCACCATCTATTTCGGTTATG

1659 CAGAAAACATCAATGTAGCAACAGAAGAAAAGTCCGTCATGCAAGCAAATGAC CAT
     || |   ||| |    |||     ||  |      ||  |   || ||  |||| |
2051 TGGACCAGTGCAAATGACGTGCAGCCCCACCCACCAGGGTGACAGCGGTTGACGGGT

1778 CCCTCGGTCTTACCACGCATACCTTAACAATGAGTACACTGTGGCCGG  ATGCCAC
     ||| |  | | ||||    |  ||  ||      |        | ||  ||  | |
2167 CCCCCAATGTCACCAAAGCTGGTTTGCTGCCAGCTCGTGAGATCCTGGTCATTTCTG

1896 CAGACAGCTTCTCTTCAGATGGTGGATTCTGTGTCTGAGGAGACTGCCTGAGAGCAC
     |||| |   | ||||  | ||  ||  ||  |   |   |  | ||| ||  ||||
2286 CGGCCGG  GCGCTTC GCTGCTGCGGCCCCAG CAGAAGGGA GCCC   CCCTTC

2016 AGTGTTCAATGTTGTCCGTTATTAGTCTGTGAcataattccagcatggtaattggtg
     ||| | | ||| |  | | || |
2397 CACACTCCA GATGGC  TAGTGAGCCTCTCCEND 2425   Matches 1212, taggtggctggggaaatagtggtggtttctttattaggtatatgaccatcagtttgg
     ggaatgggcattgtctataaattgtaatgcatatatccttctcctacttgctaagac
     tctgtggctggagatggccaatcc 2397
```

FIGURE 11C

```
CTGCCCT   GCCCACACGACAGTCGGCTTCCCTTGTGAGCTTTCTGGTGGGATTCCTGGCTT
  I  I    IIII I    I    II I       IIIIII I II   I  II   IIII II
AGAACGTGGAGCCCTCCAAATTCTCAGGGCTAATTGTGAACATTTCAGCCGGCCTCCTAGCCG

TGGAAGCCTGGAGCCTGGCTCTTCTCGCCCTGTTCCTTGTCCTCTGCGCTGCCGTCATTCTGA
  I  I   III  I    I  I I  I   II   I IIIIIIII       II I       I
GGACACTGTGGGCAGTCTTTGTAATGACAGGGTCAGTCCTCCTCTGCATGCTGGTGACAGGCA

CGTTTCTGCCGGCCTTCAGCATCCTGGTCAACATTTACTTGATGGTCCAGTTAAGTGCGGACA
 I  I II II I III IIIIIII I II IIIII II  I III I III I        II II
CCGTACTTCCTGTCTTGAGCATCTTCGTGAACATCTATCTCATGATGCAGCTGGACCAGGGCA

GCATTAGACACAGCTTGG AGGGTAAC CCCAG GGACGAAGAAGACGATGAGGATGCCTTTT
I II  I IIIII    II II II  I   I I  I I I I I  I   II   I  I
GGATCTGGCACAGTGAGGAAGCGTCCCTGGCTGCTGGCCAGGCAAAGACTCCTGACAGCAACT

CACCAAAGAAACCTCAGCTTACCTTTCATACTTCATGAAAAGACAAGTGAATGTTGATGCTGG
 II IIII  I   III III I   I         I     I   I    I I
GCCCGTAGAAGCCTGGG   ACC CTCACAATCTCTCCACTCATGCCTCAGGATCAGCTCACA

CATCGTGCTGGGCTGTCGTGGGTCTGCTGTGGACATGGCTTGCCTAACTTGTACTTCCTCCTC
 I II II  I    III III I I    II  I  II    III I III I I  I
GACAGTCCCTTGGTTTACTCATCTCCCTCTGAACAAAGAAAGCAGCCCTTCTCCTTGC CGGC

TCCTCAGCTATATGTATCCCCAAAACAGTATGTCCGTGTGCGTACATGTATGTCTGCGATGTG
IIIII    I  I I  I        I  I   III II I    II      II  I IIIII
TCCTC TCACTTGGGAAGCAGGCCTCCCTCCCTCCCTGGGACCACCCTGGCATCGCCCATGTG gcatatagtgcacacactagtaaacagtatattgctgaatagagatgtattctgtatatgtaa Mismatches 789, Unmatched 74 acatactgaaatgccatccctgtcaggatgtttaacagtggtcatgggtggggaagggataa
agcagctttcttaaacggccagggagagtgtttcttccctctgtatgacaagatgaagaggta
```

FIGURE 11D

```
Amino Terminus (Extracellular)
                     *                                                          *
  1    M V   A G F V K G M V A N W K I S E E F L K N I S A S A R E P P S E N G T S I Y
204    I V V S G F V K G S I K N W Q L T E - - K N F S C N N N D T M - V K - Y Region 1      Transmembrane 1
 40    G A G G F M P Y G F T G T L A G A A T C F Y A F V G F D C I A T T G E E V R N P
236    G E G G F M P F G F S G V L S G A A T C F Y A F V G F D C I A T T G E E V K N P Transmembrane 2
 80    Q K A I P I G I V T S L L V C F M A Y F G V S A A L T L M M P Y Y L L D E K S P
276    Q K A I P V G I V A S L L I C F I A Y F G V S A A L T L M M P Y F C L D I D S P 120    L P V A F E Y V R W G P A K Y V V A A G S L C A L S T S L L G S I P F M P R V I
316    L P G A F K N Q G W E E A K Y A V A I G S L C A L S T S L L G S M F P M P R V I Transmembrane 3
160    Y A M A E D G L L F K C L A Q I N S K T P V I A T L S G A V A A V M A F L
356    Y A M A E D G L L F K F L A K I N N R T K T P V I A T V T S G A I A A V M A F L
```

FIGURE 13A

```
                           Transmembrane 4
200  FDLKAL VDMMSTGTLMAYSLVAACVLILLRYQP)G     LCYE
396  F-LKDLV-DLMS-IG-TLLAYSLVAACVLVLRY-Q-PEQPNLVTQ 237  QPKYTPEKETLESCTMATLKSESQVTMLQ  GQGFSLRTLF
436  MARTTEELDRVDQ NELVSASESQTGFLPVAEKFSLKSIL
                                   Transmembrane 5
276  SPSAL  PTRQSASLVSFLVGFLAFLILGLSTLTTYGVQAI
475  SPKNVEPSKFSGLIVNISAGLLAALIITVCIVAVLGREAL
                                           Region 2
315  ARLEAWSLALLALFLVCAAVILT(WRQPQNQQKVAFMVP
515  AEGTLWAVFVMTGSVLLCMLVTGI-IWRQPESKTKLSFKVP
                                               Transmembrane 7
355  FLPFLPAFSILVNIYLMVQLSADTWIRFSIWMALGFLIYF
555  FVPVLPVLSIFVNIYLMMQLDQGTWVRFAVWMLIGFTIYF 395  AYGIRHSLE GNPRDEEDDEDAFSENIMVATEEKSVMQANDHHQRNLSLPFILHEKTSEC  459
595  GYGIWHSEE ASLAAGQAKTPDSNLDQCKU  623
```

FIGURE 13B

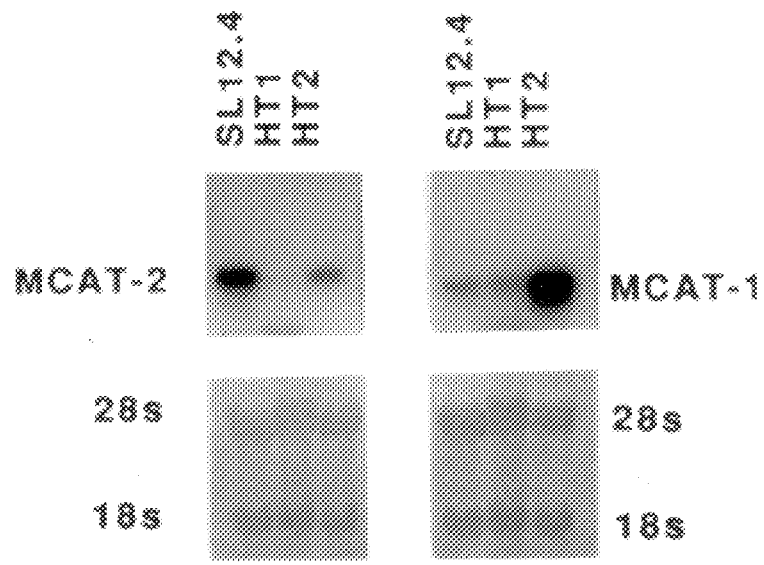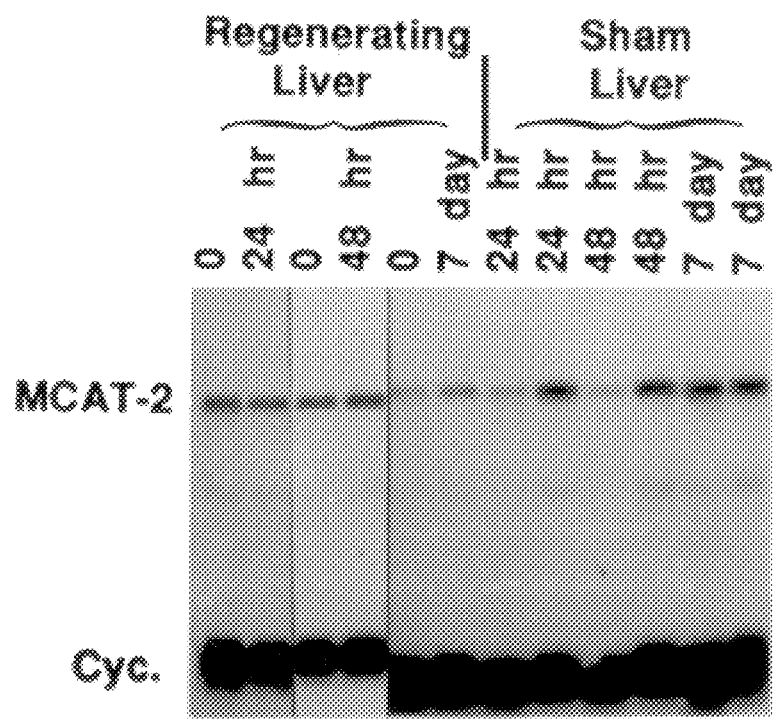
FIGURE 21

GENE ENCODING CATIONIC AMINO ACID TRANSPORTER PROTEIN

CROSS-REFERENCE TO RELATED APPLICATION

This application is a continuation-in-part of U.S. patent application Ser. No. 07/686,322, filed Apr. 11, 1991, now U.S. Pat. No. 5,312,733, which is a continuation-in-part of U.S. patent application Ser. No. 07/509,684, filed Apr. 13, 1990, now abandoned.

BACKGROUND OF THE INVENTION

1. Field of the Invention

This invention relates generally to novel DNA sequences encoding cationic amino acid transporters. More particularly, the present invention relates to novel methods of using these DNA sequences and antibodies against the proteins expressed to treat pathophysiological diseases.

2. Description of the Related Art

The $y^+$ transport system facilitates exclusively the transport of the cationic amino acids (AAs) arginine, lysine and ornithine in a sodium independent manner. An isolation of a cationic AA transporter cDNA clone (termed herein the mCAT-1 gene by Dr. J. Cunningham at Harvard Medical School has recently been reported. Other cDNA clones, isolated by more direct experiments, encode proteins that modify AA transport but are unlikely to directly transport AAs. These proteins are termed accessory or activator proteins.

The mCAT-2 gene was originally named the Tea gene. The gene is now designated murine cationic amino acid transporter (mCAT-2) because of its function as disclosed by the present invention.

Arginine is required for protein synthesis, plays a pivotal role in the biosynthesis of other AAs and is the direct precursor of urea in the urea cycle. Arginine is required for the synthesis of the primary energy phosphagen, creatine phosphate, by donating an amidine group to glycine in the first step of creatine synthesis. The liver is not a net provider of arginine due to the very high level of arginase. Arginine exchange between the kidney and the circulation requires transport mechanisms both to export arginine and import it from glomerular filtrate. Hence, every organ in the body, apart from liver and kidney, derives arginine from the plasma via transport mechanisms. In contrast, lysine is an essential AA, i.e., must be obtained from dietary sources. It is not synthesized by mammals; hence all cells must be capable of transporting lysine to carry out protein synthesis.

Arginine has potent secretagogue activities on several endocrine glands. Intravenous or oral administration of arginine to adult humans induces pituitary growth hormone, prolactin and insulin secretion. In addition, arginine has effects on the immune system independent of polyamine synthesis.

Arginine is the sole precursor for the synthesis of nitric oxide (NO). NO is the most potent vasodilator known and is essential for macrophages and T cells to carry out their normal functions. The cytotoxic activity of macrophages is dependent on NO, the production of NO in the vascular endothelium regulates blood pressure, and NO is a neurotransmitter. Like all free radicals, NO is extremely reactive and consequently highly unstable and is rapidly converted to nitrate and nitrite. NO production is regulated, in part, by IL2, TNF-alpha and INF-gamma.

The prior art remains deficient in the lack of effective mechanisms to regulate NO production. The present invention overcomes this longfelt need in the art.

SUMMARY OF THE INVENTION

In one embodiment of the present invention, there is provided a recombinant polypeptide comprising the amino acid sequence of a T cell protein encoded by the gene 20.5.

In another embodiment of the present invention, there is provided a antisera raised against two forms of the mCAT-2 protein.

In another embodiment of the present invention, there is provided a pharmaceutical composition comprising antisera raised against the mCAT-2 proteins.

In yet another embodiment of the present invention, there is provided a method of inhibiting cationic amino acid transport comprising the step of administering to a human or a non-human animal a pharmacologically effective dose of the pharmaceutical composition of the present invention.

In still yet another embodiment of the present invention, there is provided a method of inhibiting the production of nitric oxide comprising the step of administering to an animal a pharmacologically effective dose of the pharmaceutical composition of the present invention.

In a further embodiment of the present invention, there is provided a method of treating a pathophysiological state in an animal, wherein said state is characterized by production of an undesirable level of nitric oxide, comprising the step of administering a pharmacologically effective dose of the pharmaceutical composition of the present invention.

Other features, aspects and advantages of the present invention will be apparent from the following description of the presently preferred embodiments of the present invention when taken in conjunction with the following drawings.

BRIEF DESCRIPTION OF THE DRAWINGS

The following Figures are provided in order to illustrate various aspects and embodiments of the present invention. Some Figures may be in schematic form and therefore certain aspects may be exagerated in the interest of clarity and conciseness.

FIG. 3 demonstrates the DNA and predicted protein sequence of clone 20.5 (mCAT-2) cDNA. The 20.5 DNA sequence has been assigned SEQ ID No. 1 and the predicted protein sequence has been assigned SEQ ID No. 2.

FIGS. 11A–D shows the sequence alignment between 20.5 cDNA (top) and ERR cDNA (bottom). The 20.5 DNA sequence has been assigned SEQ ID No. 8 and the ERR DNA sequence has been assigned SEQ ID No. 9.

FIG. 13 shows the alignment of the mCAT-2 predicted protein sequence with the murine ecotropic retroviral receptor sequence. The mCAT2 predicted protein sequence has been assigned SEQ ID No. 2 and the ERR protein sequence has been assigned SEQ ID No. 4.

FIG. 21A shows duplicate northern blots of total RNA from SL12.4 T-lymphoma cells and two hepatoma cell lines HT1 (HT1080C), and HT2 (Hepa 1c1c7) were separately probed with mCAT-1 and -2 as indicated. The blots were stained with methylene blue to show the amount of 18s and 28s rRNA, and photographs are shown below the autoradiograms. FIG. 21B shows the total liver tissue RNA from control, regenerating liver and sham operated animals was probed with mCAT-2 and cyclophyllin (Cyc.) to compare the amount of RNA present on each filter. Each lane represents RNA from an individual animal. FIG. 21C shows a northern blot of RNA prepared with the indicated tissue RNAs was probed with a 132bp mCAT-2 fragment illustrated on the right side of C to distinguish this transcript from mCAT-2a.

DETAILED DESCRIPTION OF THE INVENTION

Figure 1:
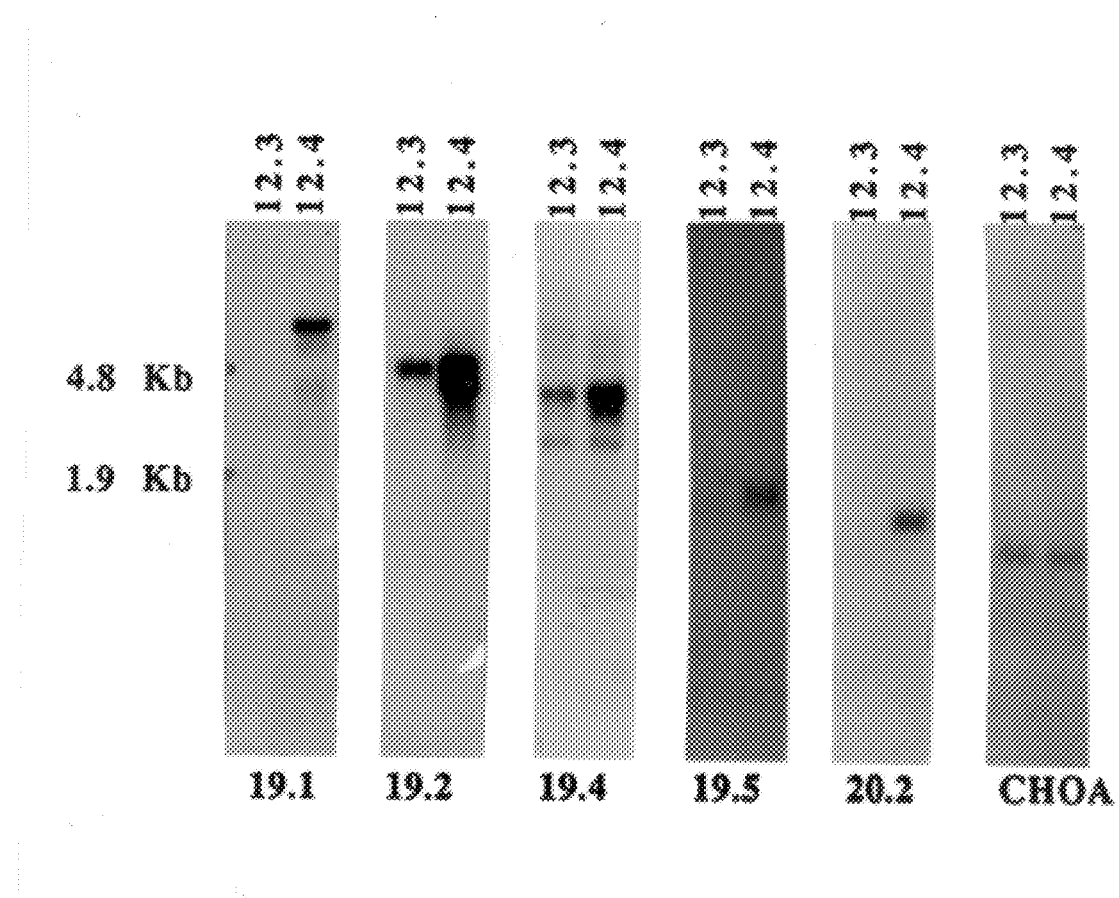
FIG. 1 demonstrates the expression of 5 different SL12.4-specific cDNA clones by northern blot.

The present invention provides novel DNA sequences and antisera which bind to these proteins. In another aspect, the present invention provides a cDNA clone, (previously referred to as 20.5 or Tea), now designated herein as the mCAT-2 gene. The mCAT-2 transcript is induced in splenocytes activated with the T cell mitogen ConA.

The DNA for this T cell protein of the present invention can be derived from any mammalian species. All that is required is that the genetic sequence for the T cell proteins (TCP) be expressed in the prokaryotic or eukaryotic organism. Preferred is the T cell DNA which expresses TCP protein(s) from mice. Especially preferred is the sequence of the T cell DNA encoding protein which is immunologically cross reactive among multiple animal species (e.g., mice, rabbit, sea lion or human).

The recombinant T cell protein may comprise the entire amino acid sequence of the T cell protein or may comprise only a specific determinant. An animal immunized with T cell recombinant protein will produce antibodies which will bind to epitopes present on the recombinant or naturally occurring polypeptides. Thus, the commercial production of T cell-containing recombinant proteins can be carried out.

Thus, the present invention makes available an anti-transmembrane T cell protein antibody for use as a probe for the transmembrane proteins of the present invention and as inhibitors of binding of the natural ligands of the transmembrane T cell proteins of the present invention and as a drug or label targeting delivery system.

The present invention provides a recombinant polypeptide comprising the amino acid sequence of a T cell protein encoded by the gene 20.5, now known as the mCAT-2 gene.

The present invention includes polyclonal antibodies raised against the protein of claim 1 and a pharmaceutical composition comprising the antisera of claim 2.

The methods of the present invention may be applied to any animal. Most preferably, the novel compositions useful in the methods of the present invention are administered to a human.

Generally, the dose of the novel antibody pharmaceutical compositions useful in the methods of the present invention is any that inhibits the production of nitric oxide in the animal. A person having ordinary skill in the art of clinical pharmacology and pharmacokinetics would readily be able to determine an appropriate dose of the novel pharmaceutical compositions of the instant invention.

Generally, the methods of treating a pathophysiological state of the present invention may be useful for any disease characterized by an undesirable level of nitric oxide production. Preferably, this method will treat diseases selected from the group consisting of sepsis, cachexia, neoplastic diseases such as Karposils sarcoma, cerebral malaria, capillary leak syndrome and autoimmune disease. Representative autoimmune diseases include systemic lupus erythematosus, rheumatoid arthritis and multiple sclerosis.

The dosage administered in the methods of the present invention is dependent upon the age, weight, kind of concurrent treatment, if any, and nature of the pathophysiological state. The effective composition useful in the methods of the present invention may be employed in such forms as capsules, tablets, liposome encapsulations, liquid solutions, suspensions or elixirs for oral administration or sterile liquid forms such as solutions, suspensions or emulsions. Any inert carrier is preferably used, such as saline or phosphate buffered saline or any such carrier in which the compounds used in the methods of the present invention have suitable solubility properties.

The novel compositions useful in methods of the present invention may be administered in a pharmaceutically acceptable carrier. The pharmaceutically acceptable carrier is any solvent with which the antibody of the present invention is compatible and which is non-toxic to the individuals treated at the amounts administered. A pharmacological dose of the novel antibody compound useful in the methods of the present invention is that amount which inhibits the production of nitric oxide.

The present invention also provides a method of inhibiting cationic amino acid transport including arginine by administering to a human or a non-human animal a pharmacologically effective dose of this pharmaceutical composition. Further, the present invention discloses a method of inhibiting the production of nitric oxide comprising the step of administering to an animal a pharmacologically effective dose of this pharmaceutical composition. There are three forms of the bidirectional cationic transporter. Any one of these can be selectively blocked to permit transport by the others. Even if one form is the predominant supplier of substrate for NO synthesis, it could be spared or blocked specifically suing the DNA protein sequences in this invention.

Having now generally described the invention, a more complete understanding can be obtained by reference to the following specific examples. These examples are provided for purposes of illustration only and are not intended to be limiting unless otherwise specified.

EXAMPLE 1

Isolation, Characterization and Culture of Cells

The isolation, characterization and culture requirements of the T lymphoma cell lines SL12.1, SL12.3, SL12.4 and somatic cell hybrids formed among them have been described in detail in Hays, et al., *Int. J. Cancer* 38:597–601 (1986); MacLeod, et al., *Cancer Research* 44:1784–1790 (1984); and MacLeod, et al., *J. Nat. Cancer Inst* 74:875–882 (1985).

The phenotypes of the SL12.3 and SL12.4 cell clones are summarized in Table 1. Transcript expression, surface protein expression, tumorigenicity and tumor type were determined by Northern analysis, flow cytometry and in vivo injection of cloned cells into syngeneic animals, respectively. TCR-β1.0 and 1.3 kb transcripts encode (D)-J-C and V-D-J-C sequences, respectively. The glucocorticoid response was determined by growth of the cells in 1 mM dexamethasome.

TABLE 1

Phenotypic Characteristics of SL12.4 and SL12.3 Cell clones

|  | SL12.4 | SL12.3 |
|---|---|---|
| Thy-1 | ++ | +++ |
| TCR- alpha | − | + |
| TCR-β |  |  |
| 1.O kb | + | − |
| 1.3 kb | − | − |
| TCR-gamma | − | − |
| TCR-delta | − | − |
| CD3-gamma | + | − |
| CD3-delta | + | − |
| CD3-epsilon | + | +/− |
| CD3-zeta | + | + |
| CD2 | + | + |
| CD4 | − | − |
| CD8 | − | − |
| Thy-1 | ++ | ++ |
| Pgp-1 | − | + |
| Surface Expression |  |  |
|  |  |  |
| ThB | + | − |
| TL | + | + |
| T20O | + | + |
| H-2K$^k$ | − | − |
| IL2r | + | + |
| Jlld | + | + |
| CD3-epsilon | − | − |
| Mel-14 | + | NT |
| Glucocorticoid Sensitivity | S | R |
| Tumorigenicity | Low | High |
| Tumor Type | Extra-Nodal | Diffuse |

R = cells resistant to lysis; S = sensitive to lysis; NT = not tested.

The lymphoma cells were cultured in Dulbecco's Modified Eagle's Medium supplemented with 10% fetal calf serum, glutamine, penicillin and streptomycin. Two human ovarian carcinoma cell lines 2008 and COLO 316 were cultured in RPMI medium 1640 supplemented with 5% bovine calf serum, glutamine and 1% Fungi-bact. When used to prepare RNA, the cells were harvested during exponential growth at a density near $5-8 \times 10^5$ cells per ml. Splenocytes derived from BALB/c mice were seeded at $3 \times 10^6$ cells/ml and stimulated with 10 μg/ml ConA for two days before harvesting the RNA.

The co-cultivation conditions for SL 12.4 cells and the thymic epithelial monolayers were as follows. Briefly, SL 12.4 cells were seeded at a density such that their final concentration after the three day co-cultivation period was $1 \times 10^6$ cells/ml. TEL or TEPI were at confluency by the third day. The cells were grown in Dubellco's Modified Eagles Medium containing 10% fetal calf serum and supplemented with glutamine and penicillin/streptomycin at 37° C.

EXAMPLE 2

Cell lines for 20.5 or mCAT-2 Expression Studies

Cell lines used in the 20.5 or mCAT-2 expression studies were embryonal carcinomas F9 and PCC4, pituitary tumor ATt20, thymic epithelial TEPI, mammary epithelial (ATCC #92) and MEF. The cells were cultured in Dulbecco's Modified Eagle's Medium supplemented with 10% fetal calf serum, glutamine, penicillin and streptomycin. Cells that were used to prepare RNA were harvested during exponential growth from cultures containing $5-8 \times 10^5$ cells per ml. Splenocytes obtained from BALB/c mice were seeded at $3 \times 10^6$ cells/ml in RPMI 1640 supplemented as above and stimulated with 10 μg/ml ConA for 6, 24, 48 or 72 hours before harvesting the RNA.

EXAMPLE 3

Cloning and Screening

Poly(A)+ mRNA from SL12.4 cells was used as a template to prepare double-stranded (ds) cDNA. EcoRI linkers were added to the dsDNA which was previously methylated. Dephosphorlyated lambda gt10 arms were ligated to the cDNA and packaged into lambda phage using Stratagene packaging extract according to the manufacturer's instructions.

Subtraction hybridization was performed essentially as follows. Single stranded cDNA was prepared from 10 mg poly(A)+ SL124 RNA using 250 $\mu$C of $^{32}$P dCTP (Amersham) in the presence of 100 ug/ml of actinomycin D and hybridized to a Rot of 1260 (mol of nucleotide per liter×sec) with 25 mg poly(A)+ RNA from SL12.3 cells in a volume of 8 ml at 68° C. for 18 hours. After hybridization, the ss cDNA was collected by chromatography through a hydroxyapatite column. From 1 $\mu$g of starting SL12.4 cDNA, approximately 120 ng (12% of the input cDNA containing 3×10$^7$ cpm) was recovered and used to probe two 150 mm nitrocellulose filters containing 20,000 lambda gt10 plaques per filter. The first of two duplicate filter lifts from the SL12.4 lambda gt10 library was probed with total cDNA from SL12.3 mRNA, and the second filter lift was probed with the SL12.4 subtraction enriched cDNA prepared as described above. The plaque purified lambda phage clones were identified as SL12.4-specific by two screenings (using separately prepared subtracted probes), subsequently Northern analysis was used to confirm that the clone hybridized only to mRNA from SL12.4 cells and not SL12.3 cells. The cDNA inserts were removed from lambda DNA by digestion with the restriction enzymes Hind III and Bgl II, isolated in low melting point agarose (Sea Kem) and subcloned into the plasmid vector pT7/T3 (Bethesda Research Laboratory) digested with Hind III and BamHI. The inserts could not be excised from the phage with EcoRI because the EcoRI sites were damaged in all of the isolates.

EXAMPLE 4

Northern blot analysis.

Total cellular RNA was isolated from cell lines and tissues by the guanidine isothiocyanate method (Maniatis, et al., In *Molecular Cloning: A Laboratory Manual*. Cold Spring Harbor Laboratory Press, Cold Spring Harbor, N.Y. (1983), modified as described (Wilkinson, et al., *EMBO J.* 7:101–109 (1988)). Briefly, for Northern analysis, 10 $\mu$g of RNA was electrophoresed in 1% agarose gels containing formaldehyde and transferred to nitrocellulose membranes.

Equal loading and transfer of RNA per lane was assessed by acridine orange staining and by hybridization with actin, CHO-A and/or cyclophillin cDNA. Northern blots were hybridized with random primed (Amersham) $^{32}$P-labeled cDNA inserts in the presence of 10% dextran sulphate and 50% formamide for 12–18 hr at 42° C., washed stepwise with a final 30 minute wash in 0.1× SSPE, 0.1% SDS at 42° or 50° C. To remove the labeled probe, RNA blots were washed with 0.1× SSPE and 0.1% SDS at 90° C., allowed to cool to room temperature, air-dried and stored under vacuum until hybridized again. For the northern blot analysis of mCAT-2 (20.5 or Tea) RNA, total cellular RNA was isolated from SL12.4, SL12.3 and fresh tissue preparations from Balb/c mice by the guanidine isothiocyanate method. Cytoplasmic or nuclear RNA was prepared as described above. For northern analysis, 10 $\mu$g of RNA was electrophoresed in 1% formaldehyde agarose gels and transferred to nitrocellulose membranes.

EXAMPLE 5

Southern blot analysis

Total cellular DNA was isolated from cells, T lymphoma and murine-hamster somatic cell hybrids and tissues from other species was digested with the restriction enzymes to the supplier's conditions. Ten $\mu$g of digested DNA was applied to each lane of a 0.7% agarose gel and electrophoresed and blotted onto Nytran supports, hybridized and washed as described for Northern blot analysis. Southern blot analysis of 20.5 was performed as above except as noted below. Total cellular DNA was isolated from SL12.4 cells, murine and hamster liver and from somatic cell hybrids. DNA from chicken and human liver was obtained commercially from Clonetec, Palo Alto, Calif. The DNA was digested with the restriction enzymes as noted. Ten $\mu$g of digested DNA was applied to each lane of a 0.8% agarose gel and electrophoresed in Tris acetate buffer for at least 48 hours and blotted onto Nytran supports, hybridized and washed as described for Northern blot analysis. The blots containing DNA from other species was washed at a lower stringency, the final wash was carried out at room temperature with 2× SSPE.

EXAMPLE 6

Isolation of novel cDNA clones using subtraction enhanced-differential screening Northern blots of RNA from SL12.3 and SL12.4 cells demonstrated that the cDNA clones isolated were differentially expressed in SL12.3 and SL12.4 cells as shown on FIG. 1. Purified inserts from the respective SL12.4 T cell specific cDNA clones were labeled and used to probe Northern blots. Each lane contained 10 $\mu$g of total cellular RNA from SL12.4 and SL12.3 cell lines as indicated. The blot was probed sequentially with the indicated radioactively labeled cDNA insert. Arrows mark the relative mobility of 18S and 28S rRNA transcripts. The amount of SL12.3 and SL12.4 RNA loaded per lane was equivalent as determined by hybridization with a CHO-A cDNA probe.

Figure 2:
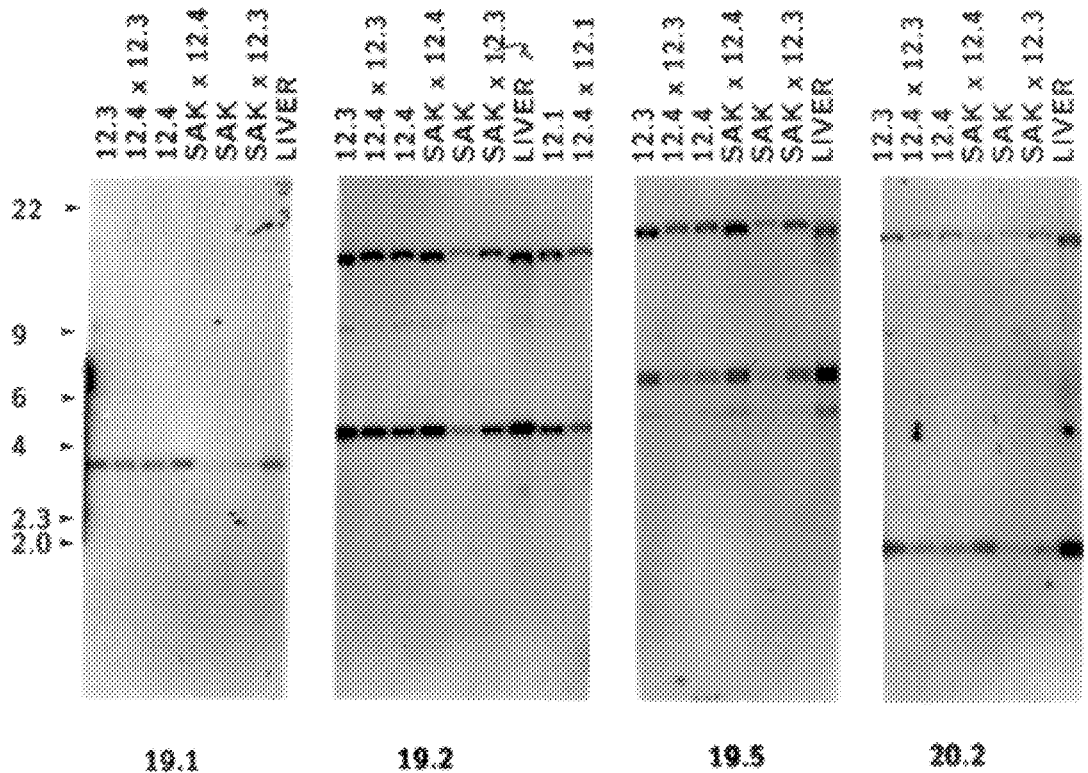
FIG. 2 demonstrates southern blot hybridization of 4 different SL12.4 specific cDNA clones.

Genomic DNA from SL12.3, SL12.4 cells and normal liver DNA was digested with EcoRI, Hind III or PstI and analyzed with purified insert probes to the cDNA clones. FIG. 2 demonstrates Southern blot hybridization of SL12.4 specific cDNA clones. Genomic DNA (10 $\mu$g per lane) from AKR mouse liver, SL12.3, SL124 and SAK cloned T lymphoma cell lines and from SL12.3×SL124, SAK× SL12.4, SAK×SL12.3 hybrid cells was digested with EcoR1 and analyzed by Southern blots hybridized with the indicated cDNA clone. Fragment sizes in kilobase pairs (determined by the co-migration of lambda Hind III digested DNA) are indicated in the margin. One or a few restriction fragments were recognized by the probes indicating that the corresponding genes are present in both cell lines at low copy number in the mouse genome. The intensity of the hybridization was similar in all the lanes indicating the genes were present in the SL12.3 cell DNA in about the same amounts and without detectable rearrangements using four different enzymes (FIG. 2). Therefore, it is likely that differences in expression of the genes in the SL12 cell clones is due to cell-specific regulation and not to the loss of, or to detectable rearrangements in the respective genes. However, small rearrangements or point mutations in SL12.3 cells cannot be ruled out. The SL12.4 specific cDNA clone 20.5 (mCAT-2) was sequenced in its entirety. The sequence is shown in FIG. 3.

EXAMPLE 7
cDNA Library construction, screening and sequence analysis

The cDNA library construction and screening for the 20.5 or mCAT-2 gene was performed as described above. The cDNA insert was removed from lambda DNA by digestion with the restriction enzymes HindIII and BglII and subcloned into the plasmid vector pT7/T3. A restriction endonuclease map was determined and fragments were subcloned into pT7T3, the plasmid purified on cesium chloride and directly sequenced by double stranded dideoxy sequencing methods using Sequenase reagents (U.S. Biochemical Corp., Cleveland, Ohio). Part of the sequence was determined using primers to the host plasmid and other specific oligonucleotide primers (17 mers) were prepared to the cDNA in the UCSD Cancer Center Core Molecular Biology Facility. Both DNA strands were sequenced in their entirety and all sequence was determined in at least two reactions performed in duplicate. Microgenie computer programs were used to assemble the overlapping sequence information and perform the initial analysis of the DNA sequence. A new cDNA library was prepared using the original mCAT-2 clone to isolate full length clones. Seven new clones were obtained.

EXAMPLE 8
Isolation and DNA sequence of the mCAT-2 or 20.5 cDNA clone

A 40,000 member SL12.4 cDNA library in lambda gt10 was screened with an SL12.4 cDNA probe subtracted against SL12.3 mRNA and simultaneously on duplicate filters with total SL12.3 cDNA as described above. This screening method was used to characterize the 20.5 gene. Based on the expression characteristics, the cDNA clone was originally been designated the Tea (T cell early activation) gene. As described below, the gene has been renamed the mCAT-2 gene. The insert from this clone was sequenced by double-stranded methods on both strands and the sequence is shown in FIG. 3. The cDNA insert is 2397 base pairs in length and contains a single long open reading frame beginning at base pair 409 and extending to 1769. The cDNA does not contain a polyadenylation signal sequence or a poly A tract. The 20.5 cDNA sequence predicts a multiple membrane-spanning protein. FIG. 3 shows the predicted 453 amino acid sequence of the predicted protein which has a molecular weight of 49.57 kilodaltons (unmodified). The cDNA sequence appeared to contain the entire coding region since the predicted N-terminal methionine codon is surrounded by a Kozak consensus sequence (GXC AUG G where X can be A,U,G or C), which is an optimal translation start site and the predicted 5' and 3' untranslated regions contain multiple stop codons in all three reading frames. This finding was later revised using new cDNA clones. The physical properties of the predicted protein were analyzed using Microgenie and PC gene programs. Three potential N-glycosylation sites are represented by stars in FIG. 4–7. The predicted protein has nine highly hydrophobic regions (underlined in FIG. 3); 7 of these have characteristics of transmembrane spanning domains based upon an analysis using IntelliGenetics software programs SOAP, HELIXMEM, NOVOTNY, and RAOARGOS.

Figure 4:
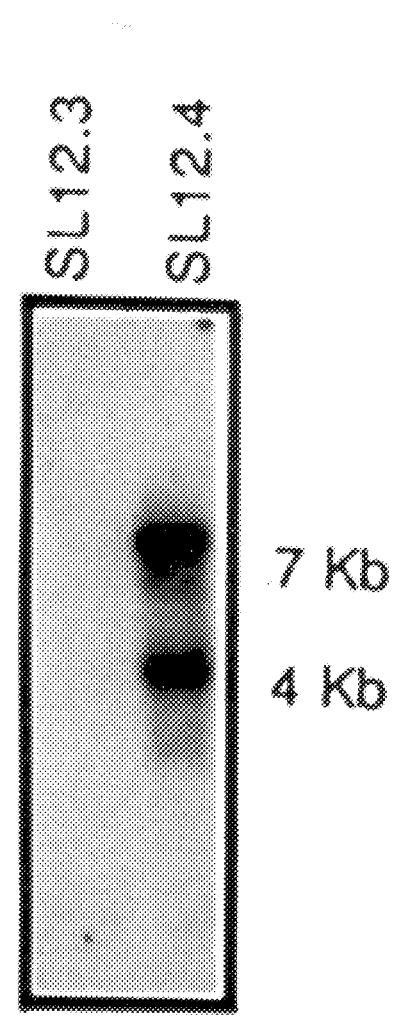
FIG. 4 demonstrates mCAT-2 (previously named Tea) gene mRNA expression in SL12.3 and SL12.4 cell lines.
Figure 5:
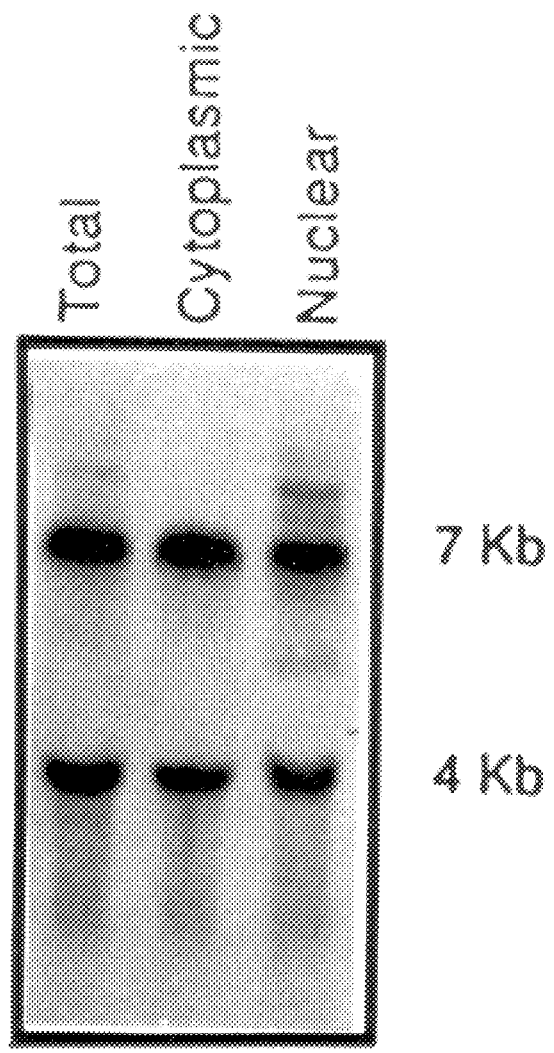
FIG. 5 shows the mCAT-2 mRNA expression in total cellular, cytoplasmic and nuclear mRNA from SL12.4 cell lines.
Figure 6:
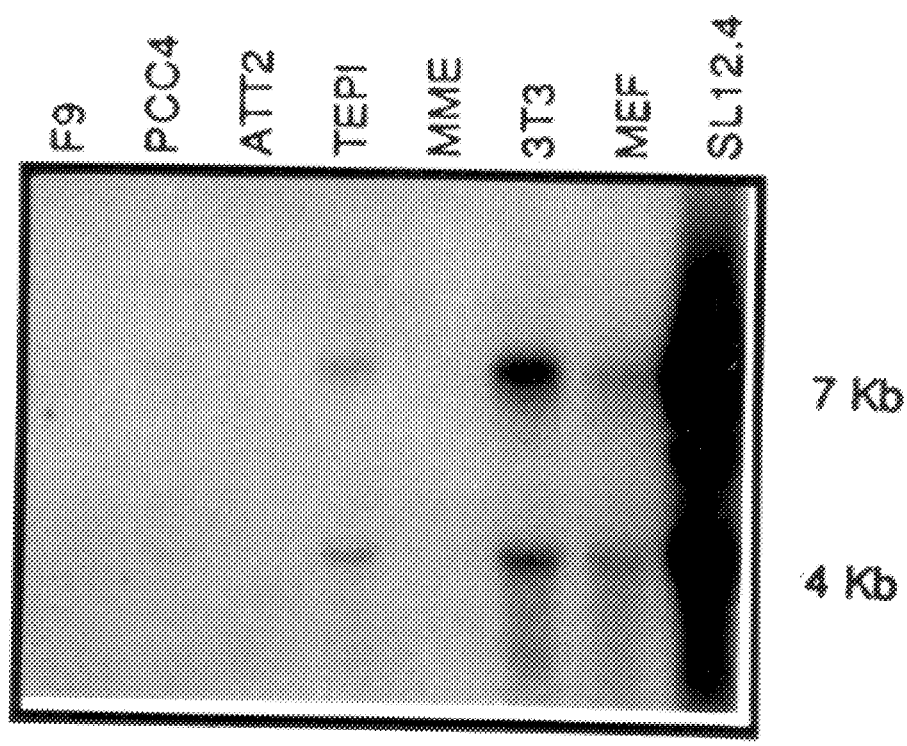
FIG. 6 shows mCAT-2 mRNA expression in a series of murine cell lines.

The Tea or mCAT-2 gene is differentially expressed in T lymphoma cells and activated T lymphoid cells from normal spleen. The expression of transcripts recognized by the 20.5 cDNA clone was assessed. FIG. 3 demonstrates the Tea gene expression. Purified insert containing the entire coding region was labeled with $^{32}$P by random priming and used to probe Northern blots in which each lane contains 10 μg of total cellular RNA (or in the case of Panel B, cytoplasmic and nuclear RNA) from SL12.4 cells, SL12.3 cells, the indicated cell lines or tissues from normal Balb/c mice. Autoradiograms of Northern blots are shown in FIGS. 4–7. FIG. 4 shows a comparison of Tea or mCAT-2 mRNA expression in SL12.3 and SL12.4 cell lines. FIG. 5 shows Tea or mCAT-2 mRNA expression in total cellular, cytoplasmic and nuclear RNA from SL12.4 cells. FIG. 6 shows Tea mRNA expression in a series of murine cell lines described in the text and FIG. 7 contains RNA from the indicated normal tissues from Balb/c mice (GALT is gut associated lymphoid tissue). The size of the transcripts in kilobases (kb) is indicated on each panel was estimated by their relative migration against BRL markers and 18 and 28S endogenous ribosomal RNA. Equivalent loading and transfer of RNA in all lanes was assessed by acridine orange staining and by hybridization with $^{32}$P-cyclophyllin (Cyc) and/or $^{32}$P-Cho-A labeled cDNA.

The 20.5 cDNA probe recognized two transcripts of approximately 4.5 kb and 8.5 kb which are present in SL12.4 cells but not in SL12.3 T lymphoma cells (FIG. 4). The subcellular location of the two transcripts was examined to determine whether they were both mature transcripts found in the cytoplasm or whether the larger RNA was a nuclear precursor. Both transcripts appear to be fully processed RNAs since they are found in the cytoplasm (FIG. 5). The origin of the two transcripts is not yet known; they could arise from alternate initiation of transcription, alternate splicing of the transcript or the utilization of alternate polyadenylation signals. Both of the mature cytoplasmic transcripts (8.5 and 4.5 kb) are larger than the cDNA clone (2.4 kb). Thus the cDNA is not full length although it does appear to contain the entire coding region. Both transcripts are detected with probes made to a 5' (nucleotide 1 to 380) and a 3' (nucleotide 2005 to 2394) region of the cDNA clone indicating that the cDNA is not a cloning artifact which joined two different transcripts. In addition to the two mature RNAs there are several larger, much less abundant transcripts present in the nuclear and total cell RNA preparations that may be unspliced or partially spliced nuclear precursors (FIG. 5). This finding led to further screening of a new SL12.4 cDNA library and the isolation of additional cDNA clones.

Several murine cell lines of embryonic (F9 and PCC4), mammary epithelial (MME) and neuronal (ATt20) origin were examined for the expression of Tea RNA. None of those cell lines express detectable Tea RNA. In contrast, cell lines of thymic epithelial (TEPI) and fibroblast (3T3, MEF) origin contain Tea mRNA, although it is much more abundant in SL12.4 T lymphoma cells (FIG. 6).

Figure 7:
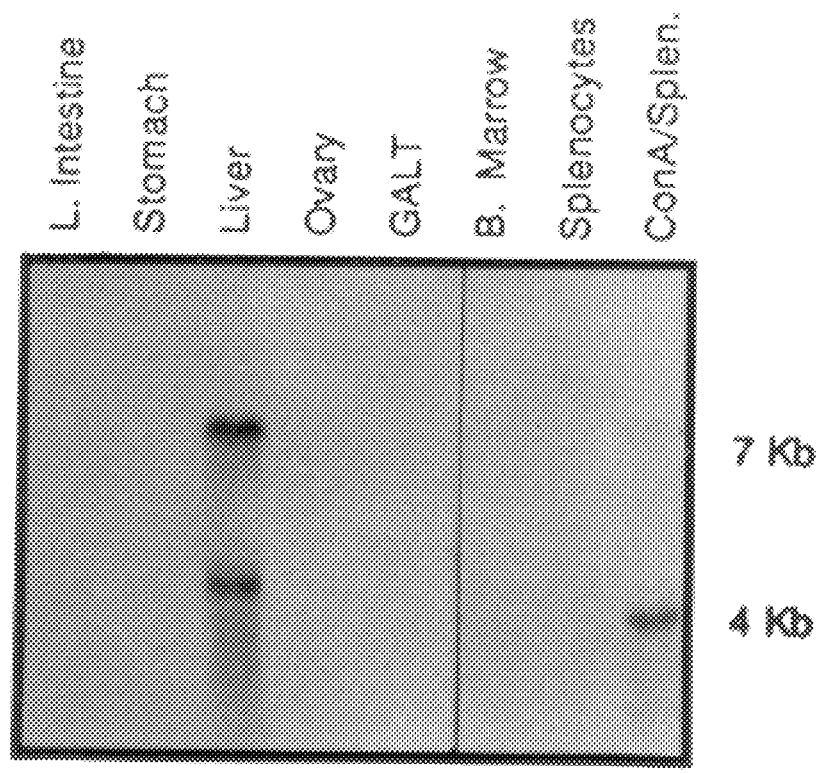
FIG. 7 shows mCAT-2 gene expression in RNA from the indicated normal tissue from Balb/c mice. GALT is gut associated lymphoid tissue.

To determine whether normal tissues and cells of the lymphoid lineage express the Tea gene, Northern blots prepared from murine tissue mRNA were examined. Cells from thymus, quiescent spleen, gut associated lymphoid tissue (GALT) and bone marrow lack detectable expression of Tea mRNA (FIG. 7). However, Tea transcripts were induced in normal spleen cells activated with the T cell mitogen Concanavalin A (ConA, FIG. 7). ConA was used to mimic the activation of splenic T cells which normally occurs in a cell clone specific manner upon appropriate presentation of foreign antigen. Liver was the only non-lymphoid tissue tested which expressed moderate amounts of Tea mRNA. Tea transcripts were undectable in intestine, stomach, ovary (FIG. 7), brain, heart, lung, kidney, pancreas or testes. Thus, the Tea gene expression is limited to a few cell types such as activated spleen cells, thymic epithelial cells, T lymphoma cells and liver.

EXAMPLE 9
Induction of Tea mRNA.

Figure 8:
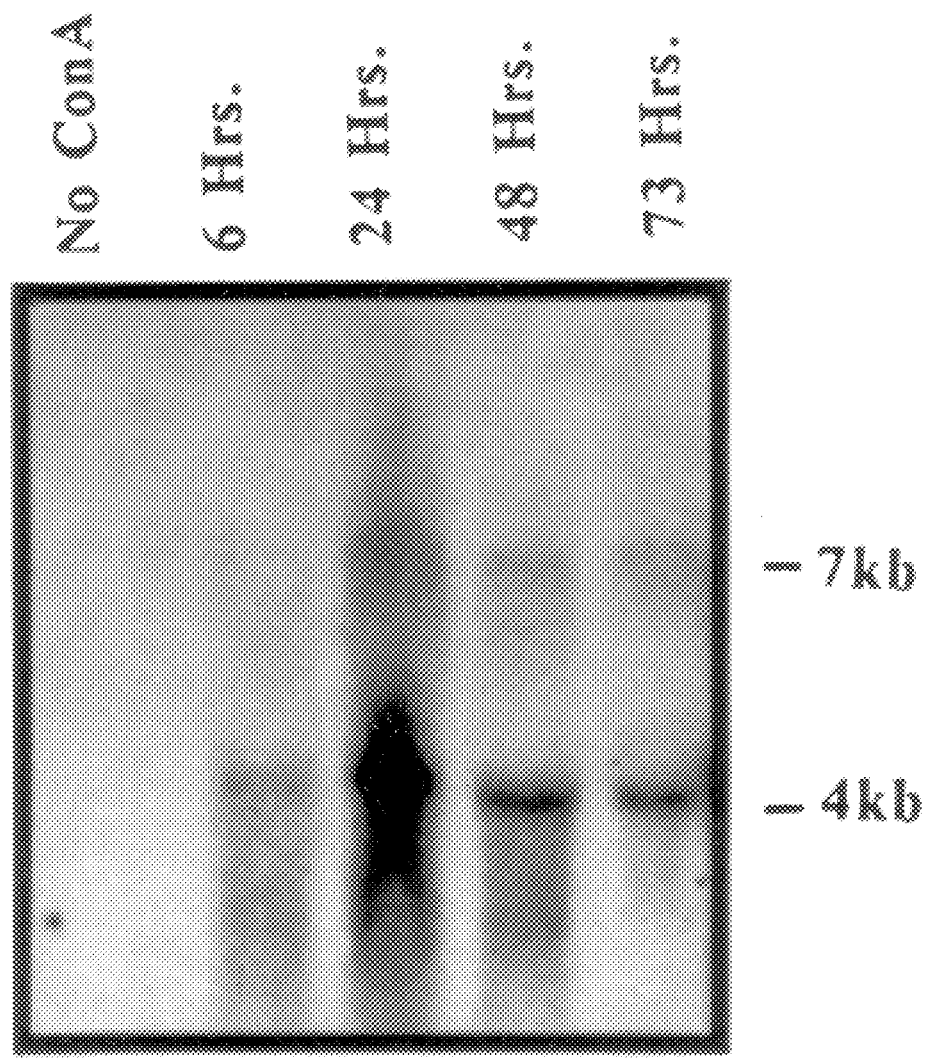
FIG. 8 shows the kinetics of mCAT-2 gene induction in activated splenocytes.
Figure 9:
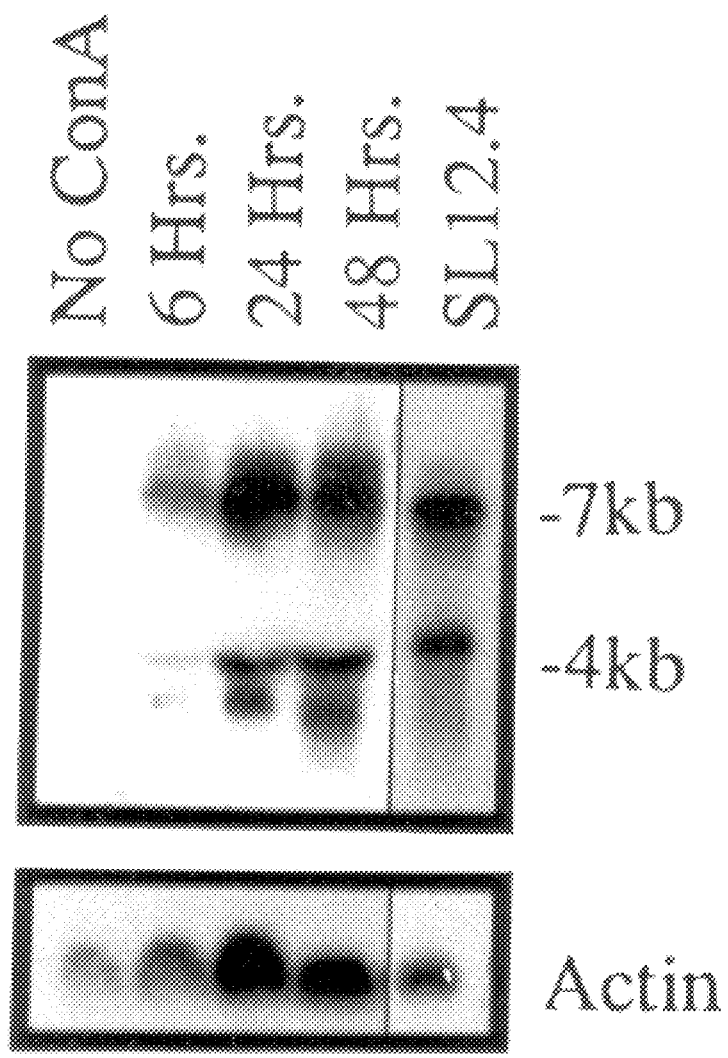
FIG. 9 shows the kinetics of Tea or mCAT-2 gene induction in activated splenocytes. The control probe indicates the relative amount of mRNA loaded in each lane.

RNA was prepared 6, 24, 48 and 72 hours after ConA was added to splenocytes. FIG. 8 shows the kinetics of Tea gene induction in activated splenocytes. Northern analysis of RNA from quiescent and activated spleen cells harvested at the indicated times following activation with the T cell mitogen Con A was performed. FIG. 8, shows a 72 hour time point, FIG. 9 show a different blot of RNA together with the control probe cyclophyllin (Cyc) to indicated the relative amount of mRNA loaded in each lane. Unlike Cyc mRNA, the rRNA load was equivalent in each lane as assessed by acridine orange staining. The Tea transcripts are not detectable in quiescent spleen lymphocytes, but becomes detectable within 6 hours, peaking at about 48 hours. Although the total amount of RNA was equivalent in each lane (10 $\mu$g), as assessed by acridine orange staining the relative ratio of ribosomal to mRNA appears to change during T cell activation since the amount of actin, CHO-A and cyclophyllin transcripts/10 $\mu$g of total RNA increases (FIG. 8). However, there is clearly an induction of Tea gene expression relative to these control RNAs during T cell activation.

EXAMPLE 10
Homology of the 20.5 DNA and AA sequence with the murine ERR

Figure 10:
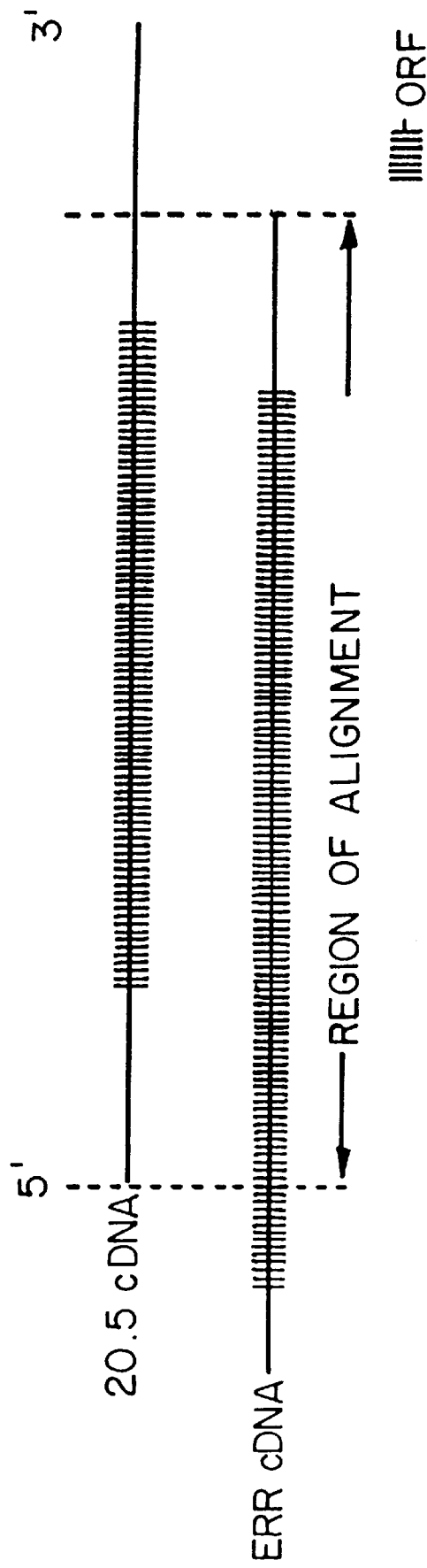
FIG. 10 demonstrates the alignment of 20.5 or mCAT-2 and ERR cDNA sequences. The 20.5 DNA sequence has been assigned SEQ ID No. 1 and the ERR DNA sequence has been assigned SEQ ID No. 3.
Figure 12:
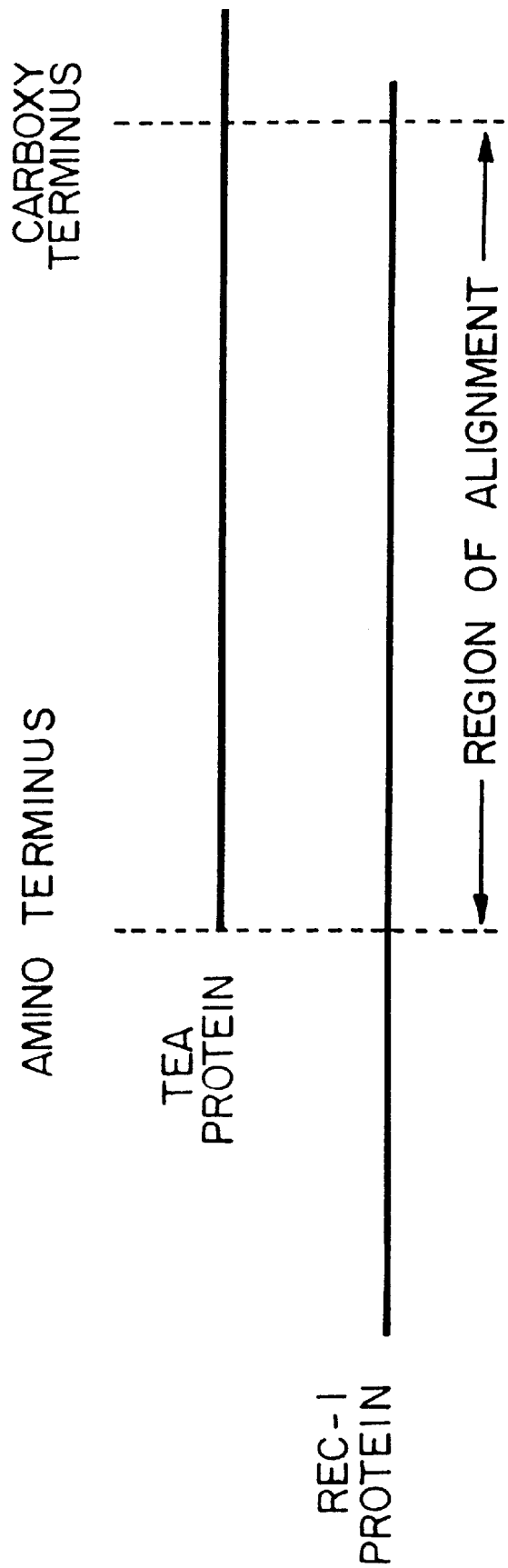
FIG. 12 demonstrates the alignment of mCAT-2 predicted protein sequence with the murine ecotropic retroviral receptor sequence. The mCAT2 predicted protein sequence has been assigned SEQ ID No. 2 and the ERR protein sequence has been assigned SEQ ID No. 4.
Figure 14:
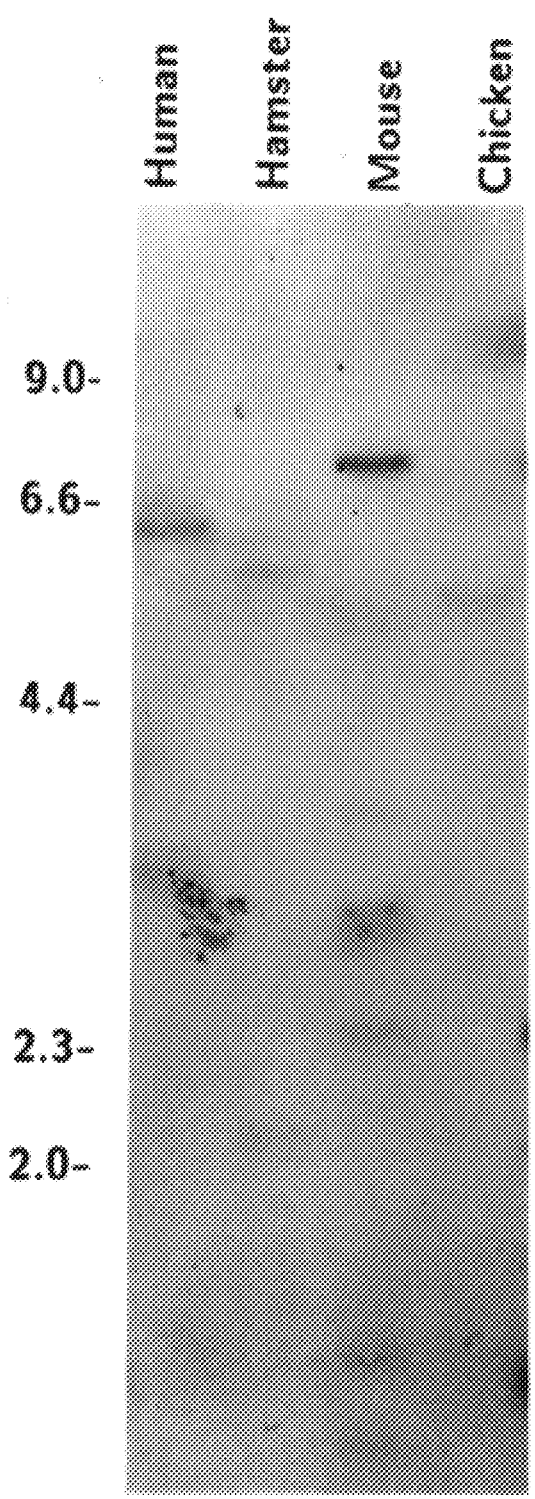
FIG. 14 demonstrates a southern analysis of DNA from different species.
Figure 15:
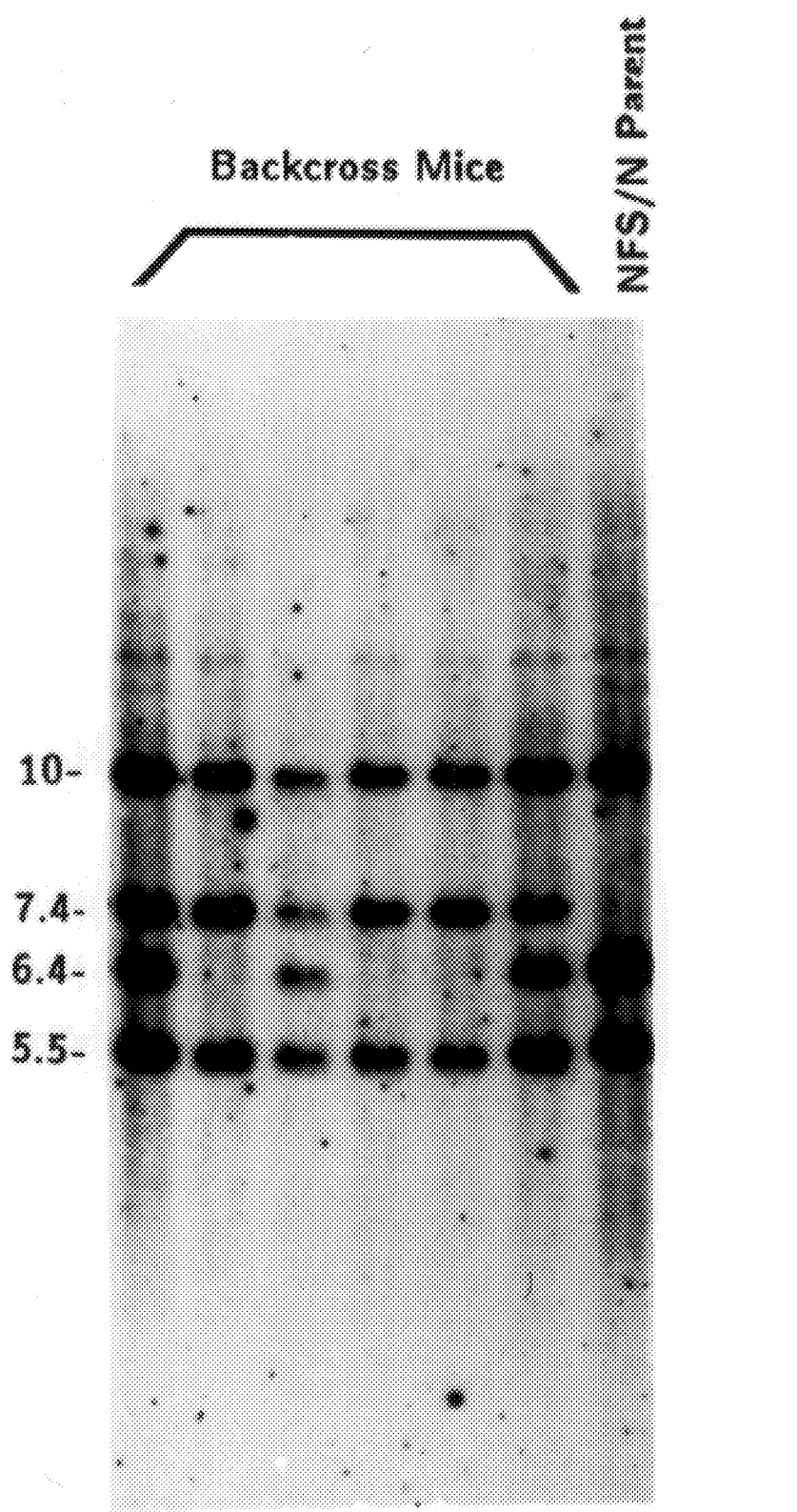
FIG. 15 shows a southern analysis of recombinant inbred DNA to position the mCAT-2 gene on chromosome 8.

Homology searches using the Bionet data base revealed no significant sequence similarity between 20.5 cDNA and other DNA sequences previously reported. However, the sequence was compared with the murine ecotropic retroviral receptor cDNA clone (ERR) and found to have extensive sequence identity. The gene which encodes the ecotropic retroviral receptor has been designated Rec-1, now renamed mCAT-1. FIG. 10 shows a comparison of the 20.5 cDNA sequence with the ERR cDNA sequence. In FIG. 10, the regions of the ERR and 20.c cDNA sequences included in the alignment analysis is indicated by the vertical lines. The open reading frames for each cDNA are indicated. In FIG. 11, the entire cDNA sequence of 20.5 is shown on the top line of each pair of lines, the cDNA sequence of ERR (bp 400–2425) lacks the first 400 base pairs and is shown on the bottom of each pair. The horizontal lines mark the positions of sequence identity. The comparison was made using Microgenie software with gaps generated to allow alignment of the most highly similar sequences. The percent identity is reported only for the the regions of cDNA which are clearly overlapping. The 20.5 cDNA is much longer at the 3' end and the ERR cDNA is much longer at the 5' end.

The sketch of the two cDNAs shows that the ERR cDNA is longer at the 5' end, while the 20.5 cDNA sequence is much longer at the 3' end; the two cDNAs are of similar overall length. The coding region of each is depicted by the cross-hatched portion of each cDNA clone. The DNA alignment reveals an overall DNA sequence identity between the overlapping regions of 20.5 cDNA (bp 1 to 2047) and ERR cDNA (bp 400 to 2425) is 59%; one region of 20.5 cDNA (bp 1011–1088) is 80% identical. The 5' noncoding region of the 20.5 cDNA sequence (bp 1 to 410) has 68% sequence identity with the overlapping 5' coding region of the ERR cDNA sequence suggesting that the two genes were derived from a common sequence through a gene duplication event.

The Tea protein has structural similarity to the ERR predicted protein derived from the ERR cDNA sequence. An alignment of the Tea protein with the ERR protein shows two regions of extensive amino acid sequence similarity (FIG. 7). FIG. 7 demonstrates the alignment of Tea protein sequence with the murine ecotropic retroviral receptor sequence. On FIG. 7, the line sketch shows the region of the two predicted protein products which were compared; the Tea protein extends from amino acid 1-404, the ERR protein from amino acid 204-603. On FIG. 13, the alignment of the two predicted proteins show the amino acid sequence predicted by the 20.5 cDNA on top, by the ERR cDNA on the bottom. The brackets delineate the borders of two regions of extensive amino acid identity; Region 1 is 81.3% identical over 192 amino acids, Region 2 shows 51.9% identity over 79 amino acids. Region 1, defined by brackets, has 81% sequence identity and 91% similarity over 193 amino acids. Region 2 has 62% sequence identity and 75% similarity over a length of 60 amino acids. Conservative amino acid differences are indicated by two dots, amino acid identities are shown by a long dash between the two.

EXAMPLE 11
Mapping of the mCAT-2 gene to Chromosome 8.

The production and characterization of Chinese hamster X mouse somatic cell hybrids has been described by Hoggan, et al., *J. Virol.* 62: 1055–1056 (1988). Briefly, NFS/N strain mice were obtained from the Division of Natural Resources, NIH, Bethesda, Md. Mus musculus mice were obtained from a laboratory colony derived from mice originally trapped in Skive, Denmark, and maintained by Dr. M. Potter, (NCI, NIH, Contract NO1-CB2-5584) at Hazelton Laboratories, Rockville, Md. Hybrid NFS/NxX. m. musculus females were backcrossed with M. m. musculus males to produce the experimental animals. DNAs were extracted from mouse livers, digested with SacI and BamHI, electrophoresed in 0.4% agarose gels for 48 hours at 24 volts and transferred to nylon membranes (Hybond N+, Amersham). Membranes were hybridized with the [$^{32}$P]-labeled 20.5 cDNA and a 438 base pair probe representing the DNA polymerase B gene which is present on Chromosome 8. Membranes were washed and probed. Kidney samples from the same mice were typed for inheritance of the markers Gr-1 and Es-1 by histochemical staining after electrophoresis on starch gels.

Since the ERR gene product functions as a viral receptor, the Tea gene was mapped to determine if it was on a chromosome known to encode one of the other known retroviral receptors. Several different somatic cell hybrids formed between Chinese hamster and mouse cells each retain a limited number of different mouse chromosomes. These hybrids were used to map the Tea gene. Southern analysis of DNAs digested with Pst I from hybrid cells demonstrated that 7 of 21 hybrids contained mouse-specific DNA fragments. A comparison of the known mouse chromosome content with the positive hybridization to mouse-specific DNA fragments indicated that the best correlation is with mouse Chromosome 8 (Table 2).

TABLE 2

Concordance between specific mouse chromosomes and the Tea gene in mouse-hamster somatic cell hybrids.

| Mouse Chromosome | Number of Hybrids DNA Hybridization per Chromosome | | | | Percent Discordancy |
|---|---|---|---|---|---|
| | +/+ | −/− | +/− | −/+ | |
| 1 | 5 | 9 | 2 | 4 | 30.0 |
| 2 | 7 | 5 | 0 | 7 | 36.8 |
| 3 | 3 | 6 | 2 | 3 | 35.7 |
| 4 | 4 | 3 | 2 | 3 | 25.0 |
| 5 | 2 | 11 | 5 | 2 | 35.0 |
| 6 | 6 | 6 | 1 | 6 | 36.8 |
| 7 | 5 | 4 | 2 | 8 | 52.6 |
| 8 | 6 | 13 | 1* | 1* | 9.5 |
| 9 | 4 | 10 | 3 | 4 | 33.3 |
| 10 | 0 | 11 | 7 | 2 | 45.0 |
| 11 | 0 | 13 | 7 | 0 | 35.0 |
| 12 | 3 | 4 | 2 | 3 | 41.7 |

TABLE 2-continued

Concordance between specific mouse chromosomes and the
Tea gene in mouse-hamster somatic cell hybrids.

| Mouse Chromosome | Number of Hybrids DNA Hybridization per Chromosome | | | | Percent Discordancy |
|---|---|---|---|---|---|
| | +/+ | −/− | +/− | −/+ | |
| 13 | 5 | 7 | 2 | 7 | 42.9 |
| 14 | 1 | 10 | 5 | 2 | 38.9 |
| 15 | 4 | 0 | 0 | 8 | 66.1 |
| 16 | 3 | 9 | 2 | 4 | 33.3 |
| 17 | 6 | 4 | 0 | 7 | 41.2 |
| 18 | 6 | 6 | 1 | 4 | 29.4 |
| 19 | 5 | 7 | 2 | 5 | 36.8 |
| X | 5 | 8 | 2 | 6 | 38.1 |

Mapping of the Tea gene using mouse-hamster somatic cell hybrids. Symbols indicate the presence (+/) or absence (−/) of the mouse Tea restriction fragment as related to the presence (/+) or absence (/−) of the particular mouse chromosome indicated by the number in the left column detected by hybridization with the 20.5 cDNA probe. The number of discordant observations is the sum of the +/− and −/+ observations.
*Neither of these hybrids were karyotyped. They were typed for other markers, thus it is possible that the +/− hybrid cell contains fragments of Chromosome 8 or a small percentage of the cells contain the chromosome. The −/+ exception may contain a portion of Chromosome 8, but lack the region containing the Tea gene.

In addition, Tea was positioned on Chromosome 8 by analysis of an interspecies backcross. DNA digested with SstI showed that NFS/N mice produce cross reactive bands of 10.0, 7.4, and 5.5 kb. M. m. musculus DNA produces 10, 6.4 and 5.5 kb, fragments. FIG. 9B shows the pattern of hybridization of the 20.5 cDNA probe in backcrosses of NFS/N×M. m. musculus F1 mice with M. m. musculus. The segregation pattern of this restriction fragment length polymorphism with other markers on Chromosome 8 demonstrated that this gene is linked to Gr-1 and Es-1 with the gene order: centromere-Polb-Gr-1-Tea-Es-1 (Tables 3 and 4).

TABLE 3

Segregation of the Tea hybridizing fragment with alleles of
Polb Gr-i and Es-1 in 57 progeny of an interspecies backcross.

| Mice | Inheritance of the NFS/N Allele | | | | Number of mice |
|---|---|---|---|---|---|
| | Polb | Gr-1 | Tea | Es-1 | |
| Parentals | + | + | + | + | 22 |
| | − | − | − | − | 13 |
| Single Recombinants | + | + | + | − | 5 |
| | − | − | − | + | 9 |
| | + | + | − | − | 0 |
| | − | − | + | + | 2 |
| | + | − | − | − | 1 |
| | − | + | + | + | 5 |

+ = Inherited the allele; − = did not inherit the allele.

TABLE 4

| Locus pair | Recombination | |
|---|---|---|
| | r/n | cM +/− S. E.[a] |
| Polb, Gr-1 | 6/57 | 10.5 +/− 4.1 |
| Gr-1, Tea | 2/57 | 3.5 +/− 2.4 |
| Tea, Es-1[b] | 14/57 | 24.5 +/− 5.7 |
| Polb, Tea | 8/57 | 14.0 +/− 4.6 |
| Gr-1, Es-1 | 16/57 | 28.0 +/− 5.9 |

TABLE 4-continued

| Locus pair | Recombination | |
|---|---|---|
| | r/n | cM +/− S. E.[a] |
| Polb, Es-1 | 22/57 | 38.6 Not Significant |

[a]Distances in centimorgans (cM) and standard error for each locus pair were calculated from the number of recombinants (r) in a sample size of n.
[b]An additional 46 mice were typed for Tea and Es-1 for a total number of recombinants of 24 in 103 backcross mice (23.3 cM +/− 4.2).

The location of the Tea gene on Chromosome 8 provides proof that the gene is distinct from the Rec-1 gene which encodes ERR and is localized to Chromosome 5. This also eliminates the possibility that Tea is the MCF retroviral receptor, which has been localized to Chromosome 1.

EXAMPLE 12
Preparation of cRNA for Microinjection.

Tea cDNA was directionally subcloned into the pSP72 plasmid (Promega) so that the 5' termini were adjacent to the SP6 promoter. The Tea-pSP72 plasmid was linearized 3' of the coding region with Sty I and transcribed in vitro using Promega (Madison, Wis.) SP6 polymerase in the presence of 0.3 mM 5' 7 meGppp5'G to cap the RNA according to manufacturer's instructions. The ERR-pSP72 (mCAT-1) was subcloned from pJet. Transcripts were assessed on agarose gels; yielding cRNA size estimates of 2.5 kb (Tea) and 1.9 and 2.4 kb (mCAT-1). The cRNA was extracted with phenol:chloroform (1:1), chloroform, and precipitated with ammonium acetate and isopropanol, dissolved in DEPC treated water at 1.0–4.0 mg/ml and used for injection into xenopus oocytes.

EXAMPLE 13
Xenopus Oocyte Microinjection

Oocytes were surgically removed from the African clawed frog *Xenopus leavis*, treated with (1.28 mg/ml) collagenase type 1A (Sigma, St. Louis, Mo.) for 2 hours in calcium free Barth's solution (see below), rinsed with calcium free Barth's solution and incubated at room temperature in calcium free Barth's for 2 hours. The oocytes were manually defolliculated and incubated at 18° C. overnight in Barth's solution (NaCl (88 mM), KCl (1 mM), NaHCO$_3$ (2.4 mM), HEPES (15 mM), Ca(NO$_3$)$_2$ 4H$_2$O (0.33 mM), CaCl$_2$ 2H$_2$O (0.41 mM), MgSO$_4$ 7H$_2$O (0.82 mM), gentamycin (10 μg/ml), pyruvic acid (3.1 mM); then injected with 30–200 ng of cRNA in 50 nl water. Oocytes were incubated at 18° C. for 2–3 days in Barth's solution.

EXAMPLE 14
Electrophysiology

Transport currents were monitored in oocytes at −60 mV using a 2-microelectrode voltage-clamp method. Recordings were made in a bath identical to Barths but without gentamycin or pyruvic acid. Amino acids were dissolved in recording solution at pH 7.3 and applied by bath exchange using a constant-flow recording chamber. Individual oocytes were prepared at several different concentrations and were applied for periods of 30 seconds preceeded and followed by washes with amino acid free recording saline. Currents were measured using an Axoclamp-2A voltage clamp (Axon Instruments, Foster City, Calif.) and tracings were recorded on a thermal chart recorder. The oocytes used had initial resting potentials of at least −45 mV. For the sodium free measurements, equimolar choline chloride was substituted for sodium chloride in the recording saline. Control oocytes were prepared from the same batch of cells as the test oocytes; they were injected with either 50 ml of DEPC water or 50 ml of in vitro transcribed GluR3 cRNA.

EXAMPLE 15
Animal Surgery

Partial hepatectomies were performed using a longitudinal incision so that approximately 60% of the liver was removed from anesthesized (70 mg/kg sodium phenobarbitol) AKR mice 6–8 weeks of age. Animals were sacrificed and RNA prepared from the liver of animals 24 hours, 48 hours and 7 days following the surgery. Total RNA made from the resected liver tissue was used as the zero time control. Nine hepatectomized animals were assessed, three for each time point. Six sham surgeries were included in the analysis.

EXAMPLE 16
Northern Analysis

Total tissue RNA was prepared from AKR mice, whereas testes tissue RNA was prepared from Balb/c nude mice. Tissues were rapidly harvested, homogenized in a 10-fold excess (weight to volume) of tissue lysis buffer and total RNA was prepared using a single step phenol extraction method. The RNA was stored in an aqueous solution containing 5% 2-mercaptoethanol, 5 mM EDTA, and 0.5% Sarkosyl at −70° C. Cell lines were cultured in Delbecco's modified Eagle's medium (DMEM high glucose), supplemented with 1% glutamine, at 37° C. in 5% $CO_2$. Cells were washed with phosphate buffered saline, lysed with ten volumes of tissue lysis buffer and total RNA prepared.

Total RNA (10 μg) from each tissue was analyzed in duplicate on a single denaturing formaldehyde/agarose gel and transferred onto NitroPlus (MSI, Westboro, Mass., 01581) membrane support. Blots were probed with random-prime labeled cDNA fragments. A specific 132 base pair probe was prepared from a BamH1/PvuII digest of the original 20.5 cDNA clone to distinguish two isoforms of mCAT-2. One half of a duplicate Northern blot was probed with a mixture of mCAT-2 (pJet 2.1 kb fragment) and cyclophyllin (0.7 kb), while the other half was probed simultaneously with Tea cDNA (2.4 kb) and cyclophyllin using identical hybridization conditions and equivalent specific activity probes. The blots were washed together with a final stringency (0.1× SSPE, 0.1% SDS at 42° C. for 30 minutes) and exposed to film for the same length of time.

EXAMPLE 17
Micro-injected oocytes transport cationic amino acids

Figure 16:
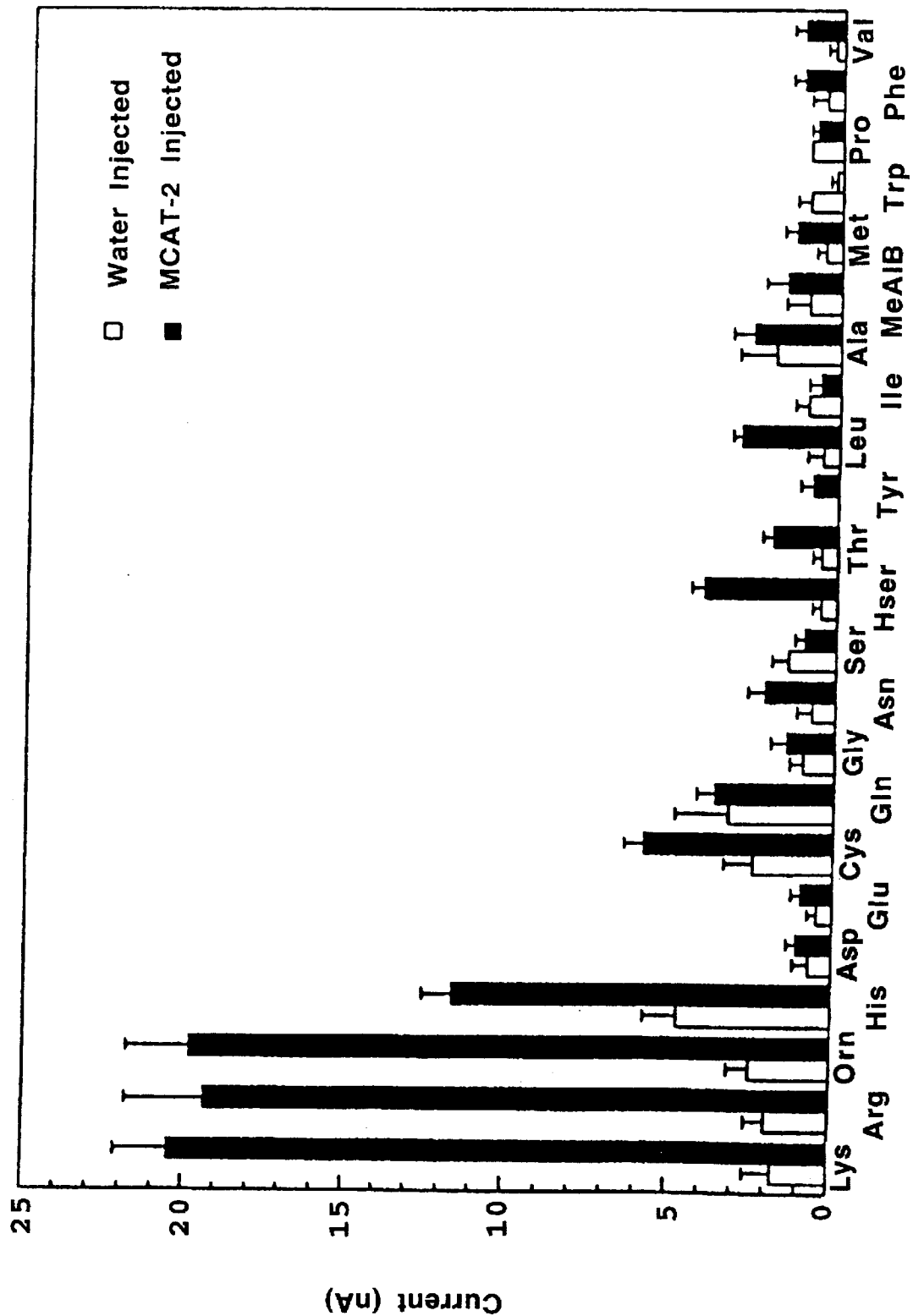
FIG. 16 demonstrates the substrate specificity of mCAT-2 mediated amino acid transport in Xenopus Oocytes. The transport was assessed by measuring inward currents recorded in response to the application of 10.0 mM of amino acid (tyrosine at 5 mM) for 30 seconds. This data was obtained from 4–14 oocytes injected with 30 or 75 ng of mCAT-2 cRNA or DEPC water. Values are the mean changes in current±SEM, holding potential at −60 mV.

FIG. 10 shows a histogram depicting the responses of cRNA and water injected Xenopus oocytes to the 20 common amino acids used for protein synthesis and to ornithine, homoserine and MeAIB [alpha-(methylamino) isobutyric acid; a system A specific substrate]. Transport was assessed by measuring membrane current changes induced by the amino acids. The Tea cRNA injected oocytes generate significant inward currents in the presence of arginine, lysine, and ornithine. Thus, the Tea cRNA encodes a protein which mediates specific transport of these cationic amino acids. For this reason, the Tea gene has been re-named mCat-2 for murine cationic amino acid transporter. The water injected controls suggest there is little endogenous transport activity since inward currents of less than 1 nA were observed with most amino acids and the largest induced current was less than 5 nA (FIG. 16). A moderate current was also noted when the oocytes were challenged with histidine at pH 7.3. It is possible that the small amount of histidine transport observed (FIG. 16) might result from the minor proportion of histidine that is cationic at pH 7.3. Only the protonated form of histidine may be recognized by this cationic transporter. Further, the transport of lysine and ornithine mediated by both mCAT-1 and mCAT-2 is indistinguishable.

Figure 17:
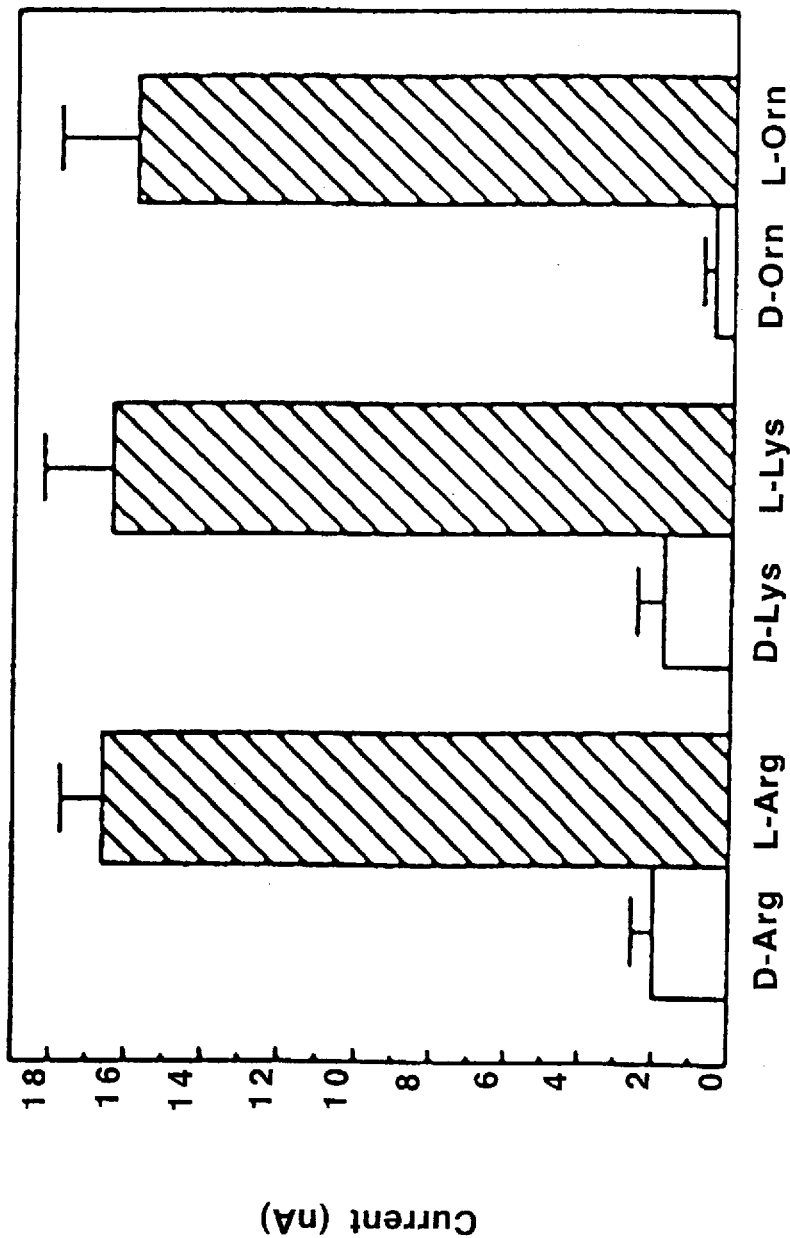
FIG. 17 demonstrates the steric specificity and sodium requirement for mCAT-2 mediated transport. The steric specificity was assessed in mCAT-2 cRNA injected oocytes (30 or 75 ng) treated with 1.0 mM L- and D-isoforms of arginine, lysine, or ornithine. The data represent the mean changes in current, ±SEM, from 5–6 different oocytes ($p<0.0001$ for arginine, lysine, and ornithine).

To examine the stereo-specificity of transport, both the L- and D- forms of the amino acids arginine, lysine and ornithine were compared. FIG. 17 shows that 1 mM concentrations of L-arginine, L-lysine, and L-ornithine generated inward currents eight times greater than those generated by the D-isomers. Thus, mCAT-2 mediated transport has specificity for the biologically active forms of its amino acid substrates.

EXAMPLE 18
mCAT-2-mediated transport is sodium independent

Figure 18:
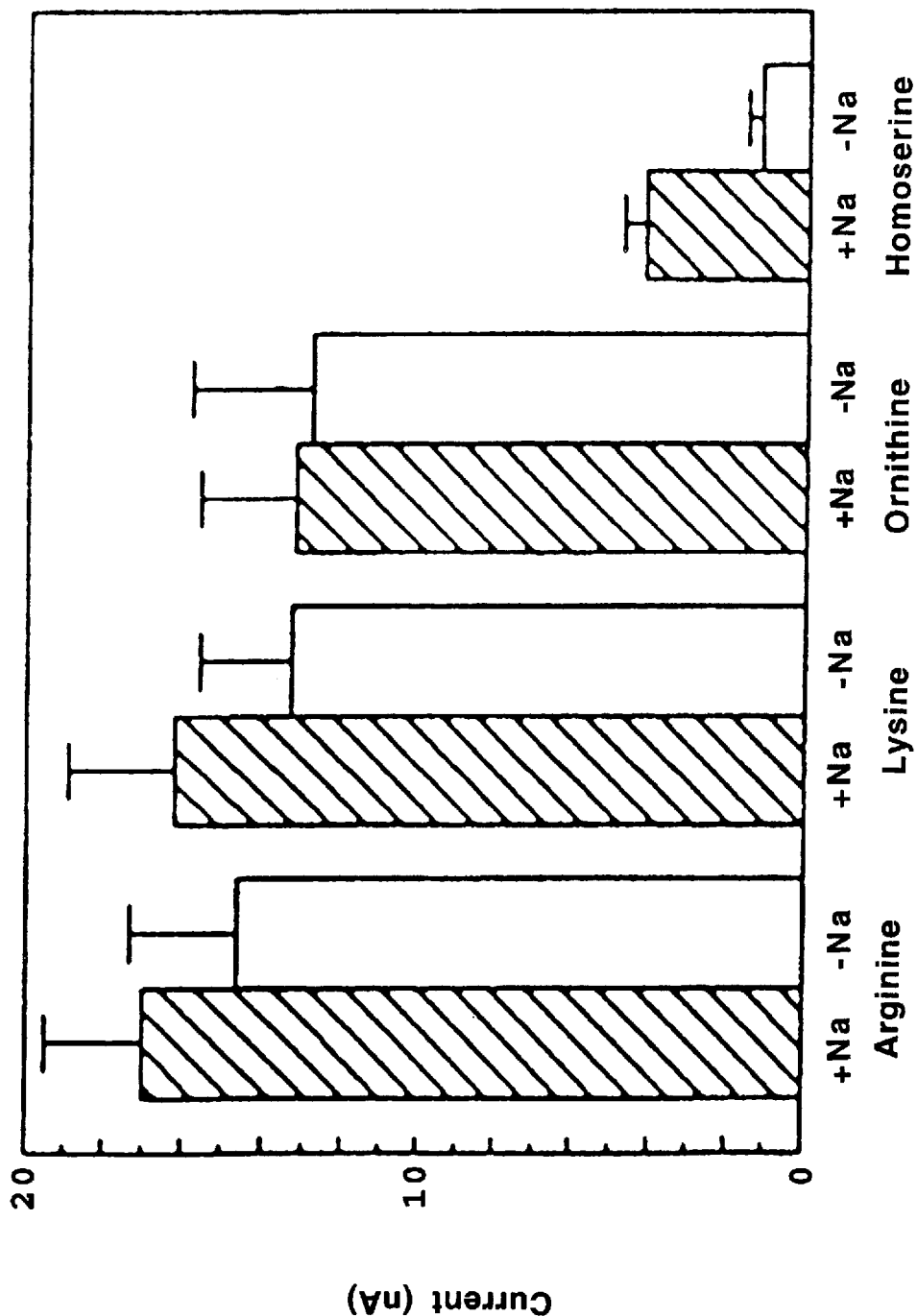
FIG. 18 shows sodium independent transport in mCAT-2 cRNA injected oocytes. Sodium dependent transport was assessed in mCAT-2 cRNA injected oocytes (30 or 75 ng) by recording the current measured in the presence and absence of sodium. Equimolar choline chloride was substituted for sodium chloride. The mean change in current±SEM was graphed using 5–6 oocytes. The holding potential was −60 mV. Arginine ($p=0.5248$), lysine ($p<0.4326$), ornithine (0.9191) at 1.0 mM and homoserine at 10.0 mM ($p<0.0025$).

Amino acid transporters appear to vary in their dependence on the transmembrane $Na^+$ gradient. Hence, the requirement of mCAT-2 for sodium ion in the transport of arginine, lysine, ornithine and homoserine was assessed in oocytes. Choline chloride was substituted for sodium chloride in the recording solution to maintain osmolarity. FIG. 18 shows arginine, lysine and ornithine are transported independent of the presence of extracellular $Na^+$. In contrast, dipolar homoserine transport is significantly sodium-dependent (p=0.0025), although the magnitude of the transport currents was quite small. (The $y^+$ system mediates cationic amino acids transport independent of sodium but requires sodium to import dipolar amino acids such as homoserine).

EXAMPLE 19
Substrate affinity and saturation of mCAT mediated transport

Figure 19A:
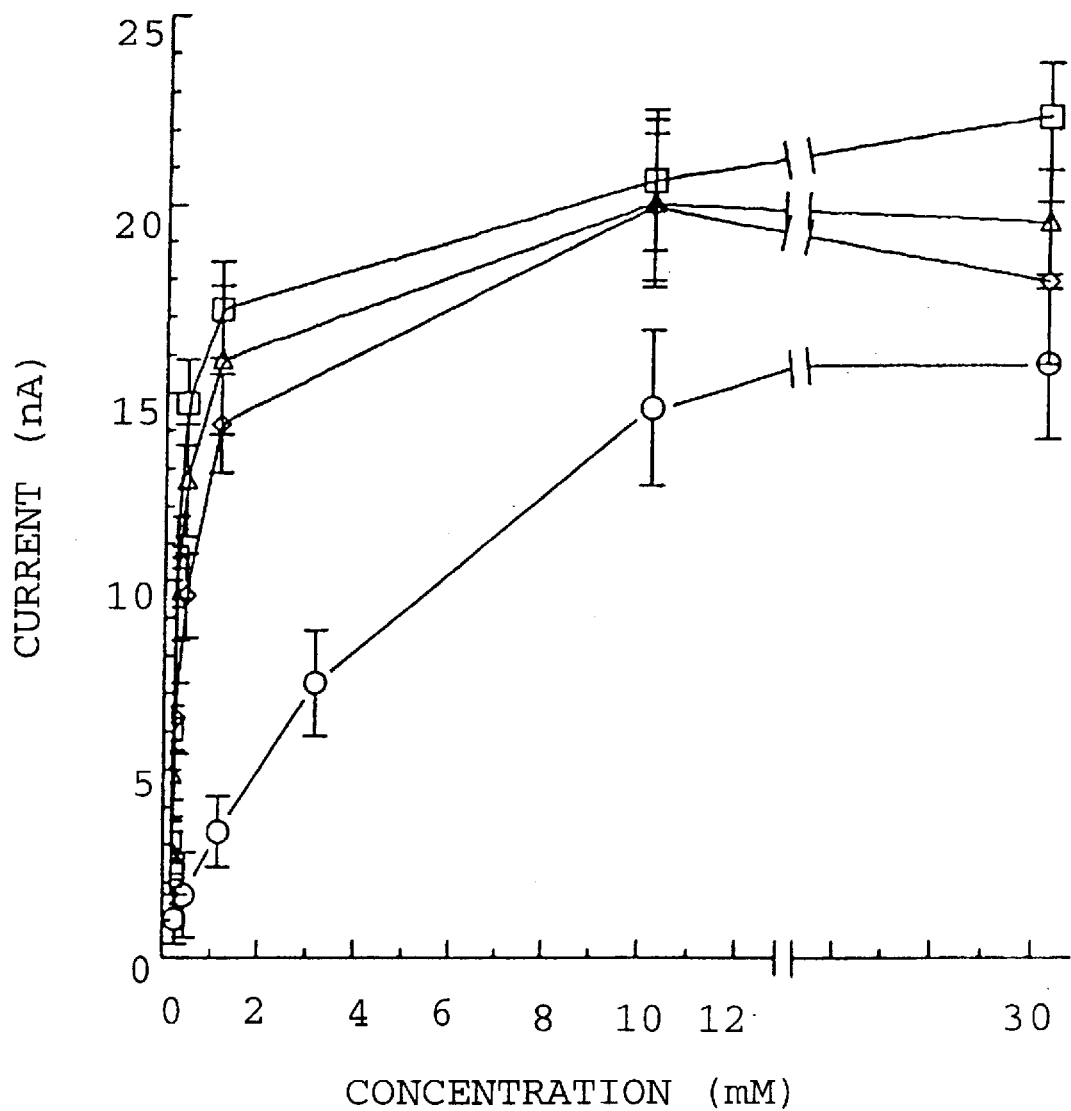
FIG. 19 shows an illustration that mCAT mediated transport is saturable. Oocytes injected with mCAT-2 cRNA were perfused with concentrations of arginine, lysine, ornithine and histidine ranging from 0.01 mM to 30.0 mM. The data represent the mean changes in current±SEM from 3–7 oocytes, previously injected with 50–200 ng mCAT-2 cRNA. Inset: Non-linear regression of the saturation data was fitted to a sigmoid curve using the GraphPad (San Diego, Calif.) program InPlot 4.03 and used in determining $I_{max}$ and $K_m$ values.

Amino acid transporters show characteristic substrate saturation properties. Saturation was observed at approximately 1 mM arginine, lysine and ornithine and 10 mM histidine (FIG. 19). As expected for system $y^+$ amino acid transporters, the concentration required to saturate the transport of the cationic amino acids arginine, lysine and ornithine is lower than that for histidine.

The apparent $K_m$ values for arginine, ornithine, lysine, and histidine were measured using concentrations of each amino acid ranging from 0.01–30 mM and shown in Table 1. These $K_m$ values were determined by non-linear regression analysis of the dose response data (FIG. 19 insert) using the GraphPad program InPlot 4.03. The mCAT-2 protein has a higher apparent affinity for arginine, lysine, and ornithine than for histidine (FIG. 13). The standard error of the mean was no greater than 2.0 for arginine, 2.4 for lysine and ornithine, and 3.8 for histidine. The apparent $K_m$ values are listed in Table 5.

TABLE 5 mCAT-2 Transports Arginine, Lysine and Ornithine with Apparent Kms similar to mCAT-1.

| Amino Acid | mCAT-2 $K_m$ mM (SEM) | mCAT-1 $K_m$ mM (SEM) |
|---|---|---|
| Arginine | 0.187 (0.028) | 0.206 (0.020) |
| Lysine | 0.203 (0.034) | |
| Ornithine | 0.419 (0.053) | |
| Histidine | 3.887 (0.099) | |

The apparent $K_m$ values for mCAT-2 were derived from the data reported in FIG. 19 and for mCAT-1 in an identical fashion, using the GraphPad program InPlot 4.03. The mCAT-1 $K_m$ value was determined using 13 oocytes;

mCAT-2 $K_m$ values were determined from 17 oocytes for arginine, 7 for lysine, 8 for ornithine, and 3 for histidine. 30–185 ng of cRNA was injected into the oocytes.

The apparent $K_m$ value derived for each amino acid was consistent among different oocytes, whereas the $I_{max}$ values tended to fluctuate. The variation in $I_{max}$ could result from different levels of mCAT-2 protein expression in individual oocytes wereas $K_m$ values are independent of the number of transporter molecules. The $I_{max}$ values are consistant for each of the amino acids tested when comparing the responses within single cells. The maximum currents generated in response to a given amino acid were not significantly different, with deviations from the mean of less than 3.5 nA for arginine, lysine, ornithine and histidine within single oocytes.

The $K_m$ value (0.187 mM) for mCAT-2 mediated arginine transport is significantly greater than the original reported value for mCAT-1 (0.07–0.077). Therefore, the apparent affinity of mCAT-1 for arginine in oocytes was determined to verify this difference in arginine affinity between the two proteins. Table 5 shows the derived arginine $K_m$ value from the experiments comparing transport mediated by either mCAT-1 (0.206 mM±0.02 SEM) or mCAT-2 (0.187 mM±0.028 SEM). There is a highly similar affinity for arginine.

EXAMPLE 20
Expression of mCAT-1 and mCAT-2 RNAs in tissues and cell lines

Figure 20:
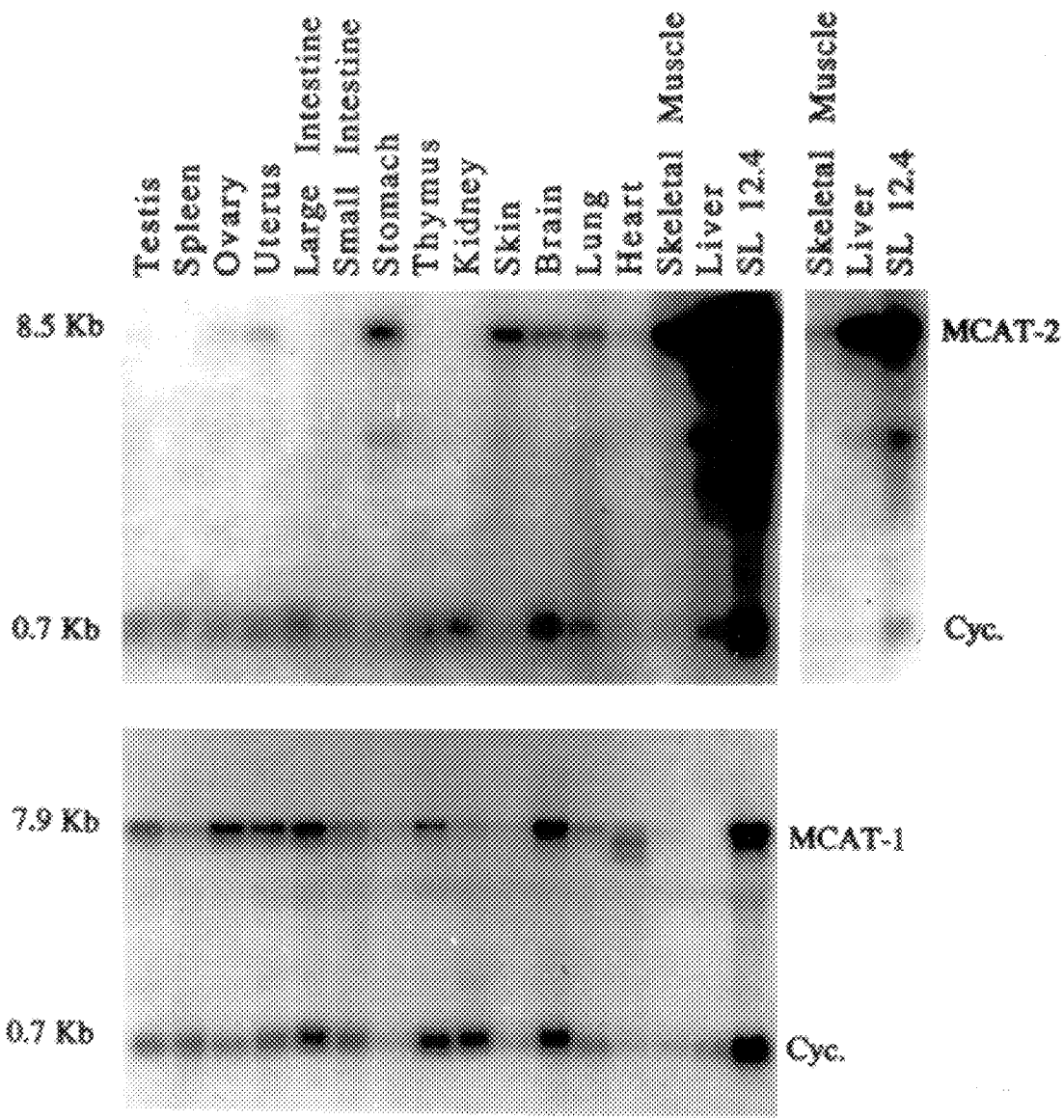
FIG. 20 shows a northern analysis of mCAT-2 and mCAT-1 transcripts in normal tissues. Total tissue RNA was prepared from adult tissues and from SL12.4 T lymphoma cells. Northern blots were prepared in duplicate and probed for the expression of either mCAT-2 or mCAT-1. A cyclophyllin probe was used to control for RNA load. A lighter exposure of mCAT-2 probed skeletal muscle, liver, and SL12.4 RNA is also shown at the right to illustrate the size of the transcript.

FIG. 20 shows the expression of both the mCAT-1 and mCAT-2 genes using n orthern analysis. mCAT-1 mRNA is detectable in all 15 tissues examined with the exception of liver. The absence of mCAT-1 protein in liver is supported by the failure of ecotropic retroviruses to infect this tissue. Two mCAT-1 transcripts of 7.9 kb and 7.0 kb were detected in ovary, uterus, large and small intestine, thymus, heart and in trace amounts in skin and skeletal muscle (only found on long exposures).

mCAT-2 RNA is most abundantly expressed in liver and at high levels in skeletal muscle. Stomach, skin, brain, lung and uterus expressed detectable mCAT-2 transcripts, while testes, ovary and heart showed only trace quantities of mCAT-2 mRNA. mCAT-2 mRNA was not detected in resting spleen lymphocytes, nor in large and small intestine, thymus or kidney.

Among the 15 tissues reported here, all express either one or both mCAT genes. mCAT-1 and mCAT-2 transcripts are co-expressed in several tissues, notably in uterus, brain, and lung. The cell lines, SL12.4 T lymphoma and two hepatoma cell lines co-express the genes (FIG. 20). In adult tissues, one gene usually predominates. For example, only mCAT-2 mRNA is expressed in liver, whereas mCAT-1 is found exclusively in intestines, resting splenic T cells and thymus.

Figure 21:
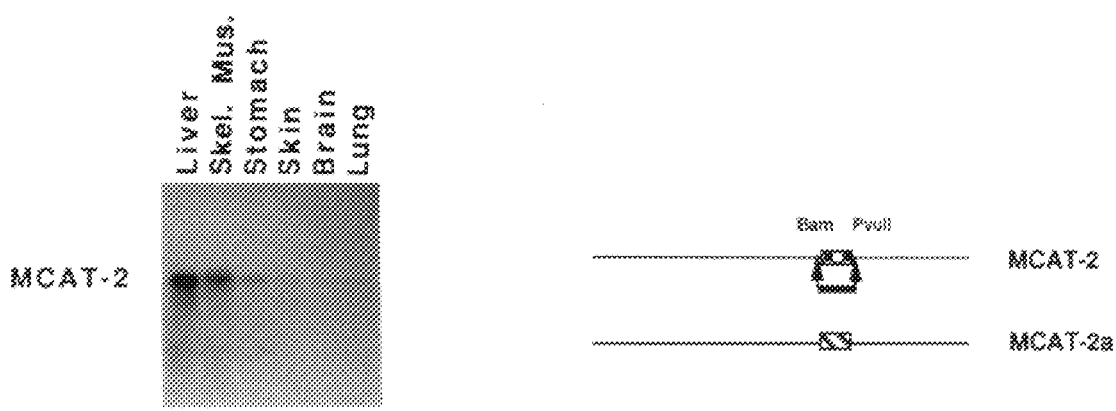
FIG. 21 shows northern analysis of mCAT-2 transcripts.

EXAMPLE 21
Normal and Regenerating Liver Express mCAT-2, but not mCAT-1 mRNA The liver, which expresses mCAT-2 constitutively, might change gene expression when in a mitogenically active state. RNA was prepared from the liver of control, sham operated and partially hepatectomized animals and the expression of both mCAT genes was examined (FIG. 20). mCAT-1 mRNA was absent from liver but is rapidly induced when liver cells are plated in culture and is present in two hepatoma cell lines shown in FIG. 21. No mCAT-1 RNA was detectable in control, sham operated or regenerating liver. In contrast, mCAT-2 RNA was expressed in control, sham operated and regenerating liver and does not appear to change substantially under conditions when liver cells are undergoing massive mitosis, 24 hours post hepatectomy (FIG. 21B).

The original isoform of mCAT-2 expressed in normal tissue, a probe specific for this region was prepared from cDNA (FIG. 21C). Northern analysis (FIG. 21C) shows that the mCAT-2 isoform is, indeed, expressed in all six tissues tested.

EXAMPLE 22
Characterization of the mCAT-2 Proteins

Each mCAT isoform contains specific sequences which might endow each transporter with a unique function. One such difference involves the carboxy termini. Both mCAT-2 isoforms share the same COOH terminal sequence which is 31 AAs longer and completely divergent from the mCAT-1 terminal sequence. The mCAT-2 protein contains a 55 AA-long carboxy terminal hydrophilic region following the last transmembrane spanning domain and is predicted to be facing the cytoplasm (MS1-3). It is sufficient to permit interaction with other intracellular proteins for signal transduction or channeling of the transported AA to a specific intracellular pool. If these carboxy termini are intracellular, they may associate with arginase in every tissue but more abundantly in the liver. The liver may express predominately the high $K_m$ transporter (mCAT-2a) in the periportal cells, to prevent arginine (or lysine) depletion from the portal blood. Regardless of whether the carboxy terminus is extracellular or intracellular, it could participate in binding to accessory molecules known to be involved in AA transport.

A second interesting difference is the AA binding domain of mCAT-2. The two mCAT-2 isoforms are identical except for a 32 AA segment generated by alternate usage of 2 exons maintaining an overall sequence identity of 97%. However, the mCAT-2a variant has a 10 fold increase in $K_m$ compared to mCAT-2 when measured in Xenopus oocytes. In contrast, the sequence homology between mCAT-1 and mCAT-2 is only 61%, yet the two transporters have identical $K_m$s and are otherwise functionally indistinguishable when expressed in Xenopus oocytes. Hence, the substantially lower affinity of mCAT-2a for arginine could indicate it serves distinct physiological functions.

EXAMPLE 23
Production of antibodies

Antibodies are produced according to the methods of Billetta and Zanetti, Immunomethods 1:41–51 (1992). Basically, t his method consists of introducing a double stranded oligonucleotide encoding a specific epitope into a highly variable (CDR3) region of a mature immunoglobulin chain which then becomes "antigenized". oligopeptides were selected representing divergent sequences of mCAT-2 and mCAT-2a. These sequences and their length were selected on 3 criteria: 1) antigenic potential, 2) sufficiently different from each other to produce antibodies specific for each epitope, and 3) when they are introduced in the variable region of the IgG chain.

Figure 22:
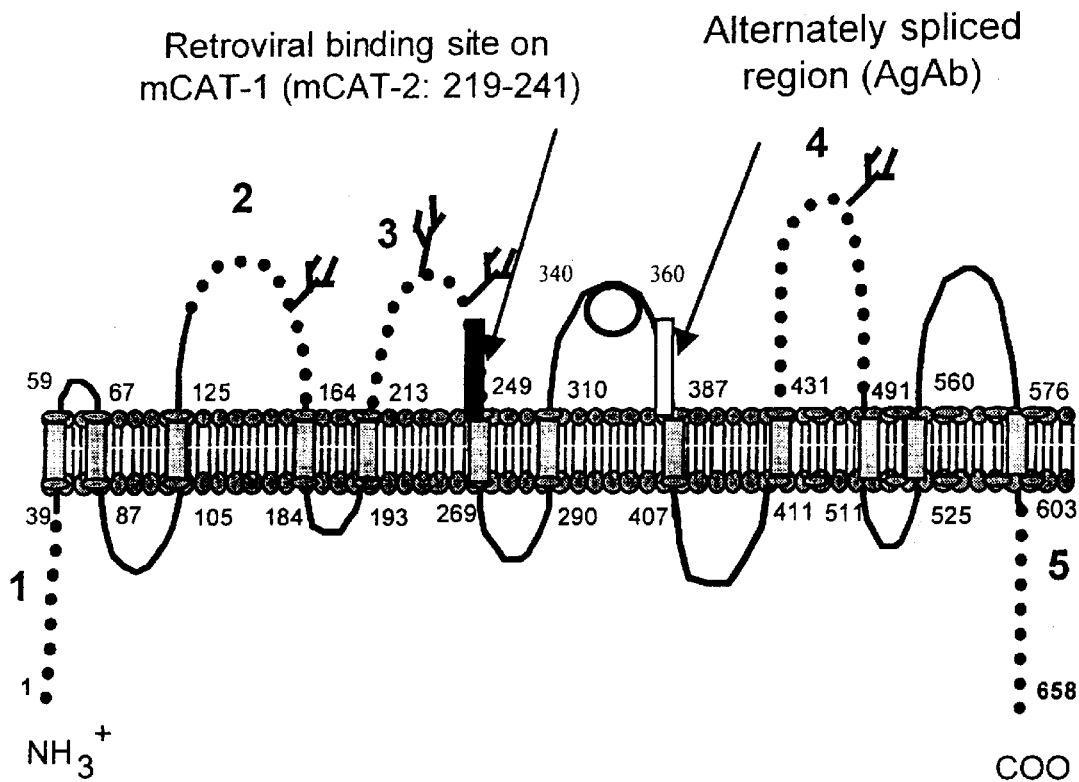
FIG. 22 shows a schematic drawing of the predicted protein structure of the mCAT-2.

A comparison of the predicted protein sequence (FIG. 22) in the ligand binding domain of the three mCAT isoforms follows:

mCAT-1   G S MF P MP R V I  Y A MA E D G L L F K F L A K I  N N R T K T P  V I  A T V T S  G A I  A    SEQ ID No. 5 mCAT-2   G S I  F P MP R V I  Y A MA E D G L L F K C L A QI  N S KT KT P V I  A T L S S  G A V A    SEQ ID No. 6 mCAT-2A  G S MF P L P R I  L F A MA R D G L L F R F L A R V – S KR QS P V A A T MT A G V I  S    SEQ ID No. 7

*  *  .  *  *  .  *  *  .  .  .  *  *  *    *  *  *  *  *  .    *  *  .  .    .  .    .  .  *  *    *  *  .  .  .  *  .  .  .

"*" indicates identical residues;
"." indicates conservative substitutions.

The region of the protein corresponding to the alternate splicing fragment is amino acids 360–400. The region for antigenized antibody contructs is amino acids 377–388. In addition, FIG. 22 also shows that the sites used for gst-mCAT-2 fusion proteins are (1) 1G or 1–33 amino acids; (2) 2B or 141–166 amino acids; (3) 3C or 212–243 amino acids; (4) 4L or 438–490 amino acids; and (5) 50 or 604–674 amino acids.

A synthetic oligonucleotide encoding the mCAT-2 sequences shown in bold above, was annealed to its complementary synthetic oligionucleotide and introduced in the CDR3 region of the productively rearranged murine $V_H62$ gene. The restriction sites were engineered so that the oligonucleotide was integrated without disrupting its own or the heavy chain reading frame. The orientation and reading frame were confirmed by sequencing. The entire CDR3 region containing the engineered mCAT fragment was excised and cloned upstream of a human gamma 1 constant region gene contained in the mammalian expression vector pNgamma1. The final construct contains the chimeric mCAT/murine/human IgG heavy chain DNA, the neomycin resistance gene, for selection of mammalian cell transformants and the ampicillin resistance gene for selection in bacteria. Similar constructs with oligonucleotides encoding mCAT-2a and mCAT-1-specific sequences have also been constructed. A fourth sequence for mCAT-2 located at the 3' end of the coding sequence has also been prepared.

Each construct was introduced by electroporation into murine J558L cells which express constitutively the murine lambda-1 light chain. G418-resistant cell clones secreting the engineered antibody were selected and expanded. The secreted antigenized antibodies were purified and used to raise antisera by classical immunization protocols.

Rabbit antisera is purified by successive affinity chromatography. The antisera is applied to human gamma-1-linked Sepharose to remove antibodies against the constant region of the human gamma-1 chain, then to murine $V_H62$-linked Sepharose to remove anti-$V_H62$ antibodies and finally to specific peptide-linked Sepharose to affinity purify the antibodies that specifically recognize individual mCAT epitopes. Antibody specificity is further examined by Western analysis of GST/mCAT and native mCAT proteins. Lysates from SL12.3 and SL12.4 cells is used as a source of native proteins. The SL12.3 cells are useful controls since they express mCAT-1 but not mCAT-2 isoforms.

What is claimed:

1. An antibody raised against a T cell protein having the seguence SEO ID No.2 encoded by the Tea gene.

\* \* \* \* \*

UNITED STATES PATENT AND TRADEMARK OFFICE
CERTIFICATE OF CORRECTION

PATENT NO. : 5,866,123
DATED : February 2, 1999
INVENTOR(S) : Carol L. MacLeod

It is certified that error appears in the above-identified patent and that said Letters Patent is hereby corrected as shown below:

In Column 2, line 7, "a" should read --an--.

In Column 2, line 38, "exagerated" should read --exaggerated--.

In Column 2, line 44, "FIG. 3 demonstrates" should read --FIG. 3A-3C demonstrate--.

In Column 3, line 1, "shows" should read --show--.

In Column 3, line 7, "mCAT2" should read --mCAT-2--.

In Column 3, line 11, "FIG. 13 shows" should read --FIG. 13A and B show--.

In Column 3, line 13, "mCAT2" should read --mCAT-2--.

Figure 19B:
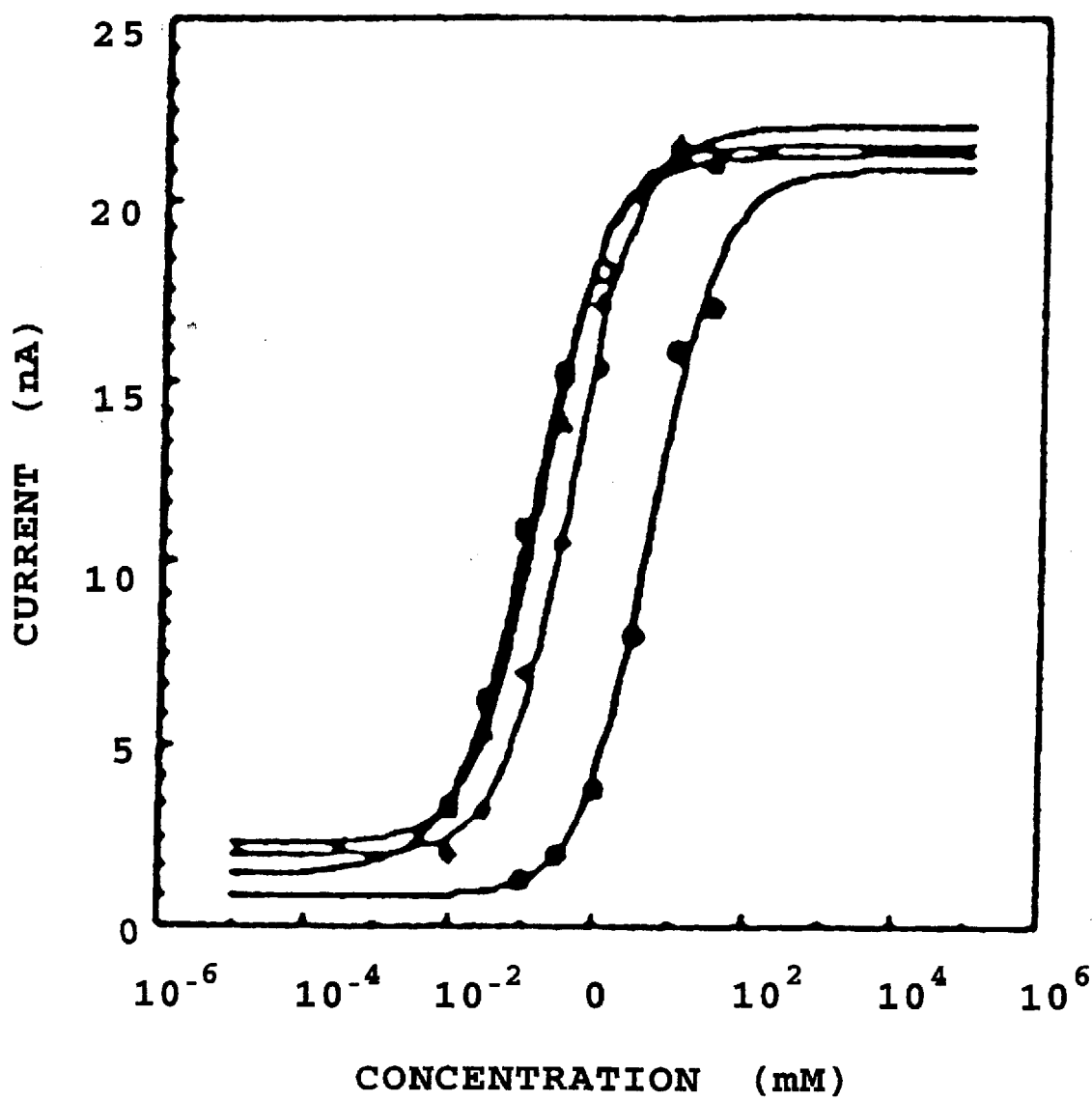

In Column 3, line 51, "Inset: Non-linear" should read --FIG. 19B shows the non-linear--.

UNITED STATES PATENT AND TRADEMARK OFFICE
CERTIFICATE OF CORRECTION

PATENT NO.  : 5,866,123
DATED       : February 2, 1999
INVENTOR(S) : Carol L. MacLeod It is certified that error appears in the above-identified patent and that said Letters Patent is hereby corrected as shown below:

In Column 3, line 52, please remove the word "was" in front of the word "fitted".

In Column 5, line 41, "suing" should read --using--.

In Column 10, line 36, "is" should read --as--.

In Column 11, line 9, "show" should read --shows--.

In Column 14, line 59, "preceeded" should read --preceded--.

In Column 17, line 8, "wereas" should read --whereas--.

In Column 17, line 9, "consistant" should read --consistent--.

In Column 17, line 31, "n orthern" should read --northern--.

UNITED STATES PATENT AND TRADEMARK OFFICE
CERTIFICATE OF CORRECTION

PATENT NO. : 5,866,123  Page 3 of 3
DATED : February 2, 1999
INVENTOR(S) : Carol L. MacLeod It is certified that error appears in the above-identified patent and that said Letters Patent is hereby corrected as shown below:

In Column 18, line 52, "t his" should read --this--.

Signed and Sealed this

Ninth Day of January, 2001

Attest:

Q. TODD DICKINSON

Attesting Officer    Commissioner of Patents and Trademarks

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
  ( A ) LENGTH: 2397 bases
  ( B ) TYPE: nucleic acid
  ( C ) STRANDEDNESS: double
  ( D ) TOPOLOGY: linear ( i i ) MOLECULE TYPE:
  ( A ) DESCRIPTION: cDNA ( i i i ) HYPOTHETICAL: No ( i v ) ANTI-SENSE: No ( v i ) ORIGINAL SOURCE:
  ( B ) STRAIN:
  ( C ) INDIVIDUAL ISOLATE:
  ( D ) DEVELOPMENTAL STAGE:
  ( F ) TISSUE TYPE:
  ( G ) CELL TYPE:
  ( H ) CELL LINE:

( x i ) SEQUENCE DESCRIPTION: SEQ ID NO:1:

GGGTGTCTTT    CCTCATCGCT    GCCCTGGCCT    CGGTTATGGC    CGGCCTTTGC    TATGCTGAAT    60

```
TTGGGGCCCG  AGTACCCAAG  ACTGGATCTG  CGTATCTATA  CACTTACGTC  ACGGTCGGAG    120
AGCTGTGGGC  CTTCATCACT  GGCTGGAATC  TCATCCTGTC  ATATGTCATA  GGTACGTCCA    180
GTGTCGCAAG  AGCATGGAGT  GGCACCTTTG  ACGAACTTCT  TAATAAACAG  ATTGGCCAGT    240
TTTTCAAAAC  GTACTTCAAA  ATGAATTACA  CTGGTCTGGC  AGAGTATCCA  GACTTCTTTG    300
CCGTGTGCCT  TGTATTACTC  CTGGCAGGTC  TTTTATCTTT  TGGAGTAAAA  GAGTCTGCTT    360
GGGTGAATAA  ATTTTTACAG  CTATTAATAT  CCTGGTCCTT  CTCTTTGTCA  TGGTGGCTGG    420
GTTTGTGAAA  GGAAATGTGG  CTAACTGGAA  GATCAGTGAA  GAGTTTCTCA  AAAATATATC    480
AGCAAGTGCT  AGAGAACCAC  CTTCTGAGAA  CGGAACAAGC  ATCTACGGGG  CTGGCGGCTT    540
TATGCCCTAT  GGCTTTACAG  GGACGTTGGC  TGGTGCTGCA  ACGTGCTTTT  ATGCCTTTGT    600
GGGCTTTGAC  TGCATTGCAA  CAACCGGTGA  AGAGGTTCGG  AATCCACAAA  AGGCGATCCC    660
CATCGGAATA  GTGACGTCCT  TACTTGTCTG  CTTTATGGCT  TACTTTGGGG  TTTCTGCAGC    720
TTTAACGCTT  ATGATGCCTT  ACTACCTCCT  GGATGAGAAA  AGTCCACTCC  CAGTCGCGTT    780
TGAGTATGTC  AGATGGGGCC  CCGCCAAATA  CGTTGTCGCA  GCAGGCTCCC  TCTGCGCCTT    840
ATCAACAAGT  CTTCTTGGAT  CCATTTTCCC  AATGCCTCGT  GTAATCTATG  CTATGGCGGA    900
GGATGGGTTG  CTTTTCAAAT  GTCTAGCTCA  AATCAATTCC  AAAACGAAGA  CACCAGTAAT    960
TGCTACTTTG  TCATCGGGTG  CAGTGGCAGC  TGTGATGGCC  TTTCTTTTTG  ACCTGAAGGC   1020
CCTCGTGGAC  ATGATGTCTA  TTGGCACCCT  CATGGCCTAC  TCTCTGGTGG  CAGCCTGTGT   1080
GCTTATTCTC  AGGTACCAAC  CTGGCTTGTG  TTACGAGCAG  CCCAAATACA  CCCCTGAGAA   1140
AGAAACTCTG  GAATCATGTA  CCAATGCGAC  TTTGAAGAGC  GAGTCCCAGG  TCACCATGCT   1200
GCAAGGACAG  GGTTTCAGCC  TACGAACCCT  CTTCAGCCCC  TCTGCCCTGC  CCACACGACA   1260
GTCGGCTTCC  CTTGTGAGCT  TTCTGGTGGG  ATTCCTGGCT  TTCCTCATCC  TGGGCTTGAG   1320
TATTCTAACC  ACGTATGGCG  TCCAGGCCAT  TGCCAGACTG  GAAGCCTGGA  GCCTGGCTCT   1380
TCTCGCCCTG  TTCCTTGTCC  TCTGCGCTGC  CGTCATTCTG  ACCATTGGA   GGCAGCCACA   1440
GAATCAGCAA  AAAGTAGCCT  TCATGGTCCC  GTTCTTACCG  TTTCTGCCGG  CCTTCAGCAT   1500
CCTGGTCAAC  ATTTACTTGA  TGGTCCAGTT  AAGTGCGGAC  ACTTGGATCA  GATTCAGCAT   1560
CTGGATGGCG  CTTGGCTTTC  TGATCTATTT  CGCCTATGGC  ATTAGACACA  GCTTGGAGGG   1620
TAACCCCAGG  GACGAAGAAG  ACGATGAGGA  TGCCTTTTCA  GAAAACATCA  ATGTAGCAAC   1680
AGAAGAAAAG  TCCGTCATGC  AAGCAAATGA  CCATCACCAA  AGAAACCTCA  GCTTACCTTT   1740
CATACTTCAT  GAAAAGACAA  GTGAATGTTG  ATGCTGGCCC  TCGGTCTTAC  CACGCATACC   1800
TTAACAATGA  GTACACTGTG  GCCGGATGCC  ACCATCGTGC  TGGGCTGTCG  TGGGTCTGCT   1860
GTGGACATGG  CTTGCCTAAC  TTGTACTTCC  TCCTCCAGAC  AGCTTCTCTT  CAGATGGTGG   1920
ATTCTGTGTC  TGAGGAGACT  GCCTGAGAGC  ACTCCTCAGC  TATATGTATC  CCCAAAACAG   1980
TATGTCCGTG  TGCGTACATG  TATGTCTGCG  ATGTGAGTGT  TCAATGTTGT  CCGTTATTAG   2040
TCTGTGACAT  AATTCCAGCA  TGGTAATTGG  TGGCATATAC  TGCACACACT  AGTAAACAGT   2100
ATATTGCTGA  ATAGAGATGT  ATTCTGTATA  TGTCCTAGGT  GGCTGGGGAA  ATAGTGGTGG   2160
TTTCTTTATT  AGGTATATGA  CCATCAGTTT  GGACATACTG  AAATGCCATC  CCCTGTCAGG   2220
ATGTTTAACA  GTGGTCATGG  GTGGGGAAGG  GATAAGGAAT  GGGCATTGTC  TATAAATTGT   2280
AATGCATATA  TCCTTCTCCT  ACTTGCTAAG  ACAGCTTTCT  TAAACGGCCA  GGGAGAGTGT   2340
TTCTTTCCTC  TGTATGACAA  GATGAAGAGG  TAGTCTGTGG  CTGGAGATGG  CCAATCC     2397
```

( 2 ) INFORMATION FOR SEQ ID NO:2:

( i ) SEQUENCE CHARACTERISTICS:
    ( A ) LENGTH: 453
    ( B ) TYPE: amino acid
    ( C ) STRANDEDNESS: single
    ( D ) TOPOLOGY: linear ( i i ) MOLECULE TYPE:
    ( A ) DESCRIPTION: protein ( i i i ) HYPOTHETICAL: yes ( i v ) ANTI-SENSE: No ( v i ) ORIGINAL SOURCE:
    ( B ) STRAIN:
    ( C ) INDIVIDUAL ISOLATE:
    ( D ) DEVELOPMENTAL STAGE:
    ( F ) TISSUE TYPE:
    ( G ) CELL TYPE:
    ( H ) CELL LINE:

( x i ) SEQUENCE DESCRIPTION: SEQ ID NO:2:

```
Met Val Ala Gly Ala Ser Ala Arg Glu Pro Pro Ser Glu Asn Gly Thr
                  5                  10                 15
Ser Ile Tyr Gly Ala Gly Gly Phe Gly Phe Asp Cys Ile Ala Thr Thr
             20                 25                 30
Gly Glu Glu Val Arg Asp Pro Gln Lys Ala Ile Pro Leu Thr Leu Met
         35                 40                 45
Met Pro Tyr Tyr Leu Leu Asp Glu Lys Ser Pro Leu Pro Val Ala Phe
 50                 55                 60
Ser Thr Ser Leu Leu Gly Ser Ile Phe Pro Met Pro Arg Val Ile Tyr
 65                 70                 75                  80
Ala Met Ala Glu Ala Thr Leu Ser Ser Gly Ala Val Ala Ala Val Met
             85                 90                 95
Ala Phe Leu Phe Asp Leu Lys Ala Leu Ile Leu Arg Tyr Gln Pro Gly
            100                105                110
Leu Cys Tyr Glu Gln Pro Lys Tyr Thr Pro Glu Lys Phe Val Lys Gly
            115                120                125
Asn Val Ala Asn Trp Lys Ile Ser Glu Glu Phe Leu Lys Asn Ile Ser
    130                135                140
Met Pro Tyr Gly Phe Thr Gly Thr Leu Ala Gly Ala Ala Thr Cys Phe
145                150                155                160
Tyr Ala Phe Val Ile Gly Ile Val Thr Ser Leu Leu Val Cys Phe Met
                165                170                175
Ala Tyr Phe Gly Val Ser Ala Ala Glu Tyr Val Arg Trp Gly Pro Ala
            180                185                190
Lys Tyr Val Val Ala Ala Gly Ser Leu Cys Ala Leu Asp Gly Leu Leu
            195                200                205
Phe Lys Cys Leu Ala Gln Ile Asn Ser Lys Thr Lys Thr Pro Val Ile
    210                215                220
Leu Val Asp Met Met Ser Ile Gly Thr Leu Met Ala Tyr Ser Leu Val
225                230                235                240
Ala Ala Cys Val Glu Thr Leu Glu Ser Cys Thr Asn Ala Thr Leu Lys
                245                250                255
Ser Glu Ser Gln Asn Thr Met Leu Gln Gly Gln Gly Phe Ser Leu Arg
            260                265                270
Thr Leu Phe Ser Pro Ser Ala Leu Pro Thr Arg Gln Ile Leu Thr Thr
            275                280                285
Tyr Gly Val Gln Ala Ile Ala Arg Leu Glu Ala Trp Ser Leu Ala Leu
```

|   |   |   |   |   | 290 |   |   |   |   | 295 |   |   |   |   | 300 |   |   |   |   |
|---|---|---|---|---|---|---|---|---|---|---|---|---|---|---|---|---|---|---|---|
| Asn | Gln | Gln | Lys | Val | Ala | Phe | Met | Val | Pro | Phe | Leu | Pro | Phe | Leu | Pro |
| 305 |   |   |   |   | 310 |   |   |   |   | 315 |   |   |   |   | 320 |
| Ala | Phe | Ser | Ile | Trp | Met | Ala | Leu | Gly | Phe | Leu | Ile | Tyr | Phe | Ala | Tyr |
|   |   |   |   | 325 |   |   |   |   | 330 |   |   |   |   | 335 |   |
| Gly | Ile | Arg | His | Ser | Leu | Glu | Gly | Glu | Lys | Ser | Val | Met | Gln | Ala |
|   |   |   | 340 |   |   |   |   | 345 |   |   |   | 350 |   |   |
| Asn | Asp | His | His | Gln | Arg | Asn | Leu | Ser | Leu | Pro | Phe | Ser | Ala | Ser | Leu |
|   |   | 355 |   |   |   | 360 |   |   |   |   | 365 |   |   |   |
| Val | Ser | Phe | Leu | Val | Gly | Phe | Leu | Ala | Phe | Leu | Ile | Leu | Gly | Leu | Ser |
|   | 370 |   |   |   |   | 375 |   |   |   |   | 380 |   |   |   |
| Leu | Ala | Leu | Phe | Leu | Val | Leu | Cys | Ala | Ala | Val | Ile | Leu | Thr | Ile | Trp |
| 385 |   |   |   |   | 390 |   |   |   |   | 395 |   |   |   |   | 400 |
| Arg | Gln | Pro | Gln | Leu | Val | Asn | Ile | Tyr | Leu | Met | Val | Gln | Leu | Ser | Ala |
|   |   |   |   | 405 |   |   |   |   | 410 |   |   |   |   | 415 |   |
| Asp | Thr | Trp | Ile | Arg | Phe | Ser | Ile | Asn | Pro | Arg | Asp | Glu | Glu | Asp | Asp |
|   |   |   | 420 |   |   |   |   | 425 |   |   |   | 430 |   |   |
| Glu | Asp | Ala | Phe | Ser | Glu | Asn | Ile | Asn | Val | Ala | Thr | Ile | Leu | His | Glu |
|   |   | 435 |   |   |   | 440 |   |   |   |   | 445 |   |   |   |
| Lys | Thr | Ser | Glu | Lys |
|   |   | 450 |   | 453 |

( 2 ) INFORMATION FOR SEQ ID NO:3:

( i ) SEQUENCE CHARACTERISTICS:
        ( A ) LENGTH: 1591
        ( B ) TYPE: nucleic acid
        ( C ) STRANDEDNESS: double
        ( D ) TOPOLOGY: linear ( i i ) MOLECULE TYPE:
        ( A ) DESCRIPTION: cDNA ( i i i ) HYPOTHETICAL: No ( i v ) ANTI-SENSE: No ( v i ) ORIGINAL SOURCE:
        ( B ) STRAIN:
        ( C ) INDIVIDUAL ISOLATE:
        ( D ) DEVELOPMENTAL STAGE:
        ( F ) TISSUE TYPE:
        ( G ) CELL TYPE:
        ( H ) CELL LINE:

( x i ) SEQUENCE DESCRIPTION: SEQ ID NO:3:

| ATCTCCTTCT | TGATTGCTGC | TCTCGCCTCC | GTGCTGGCCG | GCCTGTGCTA | 50 |
| CGGCGAGCTT | TGGGCCTTCA | TCACTGGCTG | GAACCTGATT | CTCTCCTACA | 100 |
| TCATCGGTAC | TTTCTCACGT | CAGCACATGG | CCCTGAATGC | TCCTGGGGTG | 150 |
| CTGGCCCAAA | CCCCGGACAC | CATGGTCAAC | AAAATTTTCA | CCTGTATCAA | 200 |
| TGTCCTGGTC | TTGTGCTTCA | TCGTGGTCTC | CTGTAACAAC | AACGACACAA | 250 |
| ACGTGAAATA | CGGTGAGGTC | GTGGGCTTTG | ACTGCATCGC | CACCACAGGG | 300 |
| GAAGAAGTCA | AGAACCCCCA | GAAGGCCGCT | CTCACGCTCA | TGATGCCTTA | 350 |
| CTTCTGCCTG | GACATCGACA | GCCCGCTGCC | TGCACTTTCC | ACCAGTCTCC | 400 |
| TAGGCTCCAT | GTTTCCCATG | CCCCGAGTTA | TCTATGCCAT | AATCGCCACT | 450 |
| GTGACCTCAG | GCGCCATTGC | TGCTGTGATG | GCCTTCCTCT | TGAACGTGT | 500 |
| TTTGGTCTTA | CGGTACCAGC | CAGAACAACC | TAATCTGGTA | TACCAGATGG | 550 |

| | | | | |
|---|---|---|---|---|
| CCAAGTTTGG | TGCCCCTGTC | CCCAAGACGG | GCTCAGCCTA | CCTCTACAGC | 600 |
| TACGTGACGG | TGGGGGCAAG | CGTGGCAAGA | GCCTGGAGTG | CGACTTTTGA | 650 |
| CGAGCTGATA | GGCAAGCCCA | TCGGAGAGTT | ATTTGCTGTG | ATTATAATTA | 700 |
| TCATCTTAAC | AGGACTGTTA | ACTCTTGGCG | TGAAGGAGTC | AGTGTCCGGG | 750 |
| TTCGTGAAAG | GCTCCATTAA | AAACTGGCAG | CTCACGGAGA | AAAATTGAGG | 800 |
| GTTTATGCCC | TTTGGATTCT | CTGGTGTCCT | GTCAGGGGCA | GCGACCTGCT | 850 |
| TTTATGCCTC | CATTCCTGTG | GGCATCGTGG | CGTCCCTCCT | CATTTGCTTC | 900 |
| ATAGCGTACT | TTGGCGTGTC | CGGTGCCTTC | AAGCACCAGG | GCTGGGAAGA | 950 |
| AGCTAAGTAC | GCAGTGGCCA | TTGGCTCTCT | CTGCGTGGCT | GAAGATGGAC | 1000 |
| TACTGTTTAA | ATTTTTGGCC | AAAATCAACA | ATAGGACCAA | ACACCCGTG | 1050 |
| AAGGACCTGG | TGGACCTCAT | GTCCATTGGC | ACTCTCCTGG | CTTACTCTTT | 1100 |
| GGTGGCTGCC | TGAACCACCG | AGGAGCTAGA | TCGAGTAGAT | CAGAATGAGC | 1150 |
| TGGTCAGTGC | CAGTGAATCA | CAGACAGGCT | TTTTACCGGT | AGCCGAGAAG | 1200 |
| TTTTCTCTGA | AATCCATCCT | CTCACCCACT | CTTATCATCA | CCGTGTGCAT | 1250 |
| TGTGGCCGTG | CTTGGAAGAG | AGGCCCTGGC | CGAAGTCATC | TGGAGACAGC | 1300 |
| CTGAGAGCAA | GACCAAGCTC | TCATTTAAGG | TACCCTTTGT | CCCGTGGGTC | 1350 |
| CGGTTTGCAG | TGTGGATGCT | GATAGGTTTC | ACCATCTATT | TCGGTTATGT | 1400 |
| GGACCAGTGC | AAATGACGTG | CAGCCCCACC | CACCAGGGTG | ACAGCGGTTG | 1450 |
| ACGGGTCCCC | CAATGTCACC | AAAGCTGGTT | TGCTGCCAGC | TCGTGAGATC | 1500 |
| CTGGTCATTT | CTGCGGCCGG | GCGCTTCGCT | GCTGCGGCCC | CAGCAGAAGG | 1550 |
| GAGCCCCCCT | TCCACACTCC | AGATGGCTAG | TGAGCCTCTC | C | 1591 |

( 2 ) INFORMATION FOR SEQ ID NO:4:

( i ) SEQUENCE CHARACTERISTICS:
        ( A ) LENGTH: 419
        ( B ) TYPE: amino acid
        ( C ) STRANDEDNESS: single
        ( D ) TOPOLOGY: linear ( i i ) MOLECULE TYPE:
        ( A ) DESCRIPTION: protein ( i i i ) HYPOTHETICAL: No ( i v ) ANTI-SENSE: No ( v i ) ORIGINAL SOURCE:
        ( B ) STRAIN:
        ( C ) INDIVIDUAL ISOLATE:
        ( D ) DEVELOPMENTAL STAGE:
        ( F ) TISSUE TYPE:
        ( G ) CELL TYPE:
        ( H ) CELL LINE:

( x i ) SEQUENCE DESCRIPTION: SEQ ID NO:4:

| Ile | Val | Val | Ser | Gly | Phe | Val | Lys | Gly | Ser | Ile | Lys | Asn | Trp | Gln | Leu | Thr |
|---|---|---|---|---|---|---|---|---|---|---|---|---|---|---|---|---|
| | | | | 5 | | | | | 10 | | | | | 15 | | |

| Glu | Lys | Asn | Phe | Ser | Cys | Asn | Asn | Asn | Asp | Thr | Met | Val | Lys | Tyr | Gly | Glu |
|---|---|---|---|---|---|---|---|---|---|---|---|---|---|---|---|---|
| | | 20 | | | | | 25 | | | | | 30 | | | | |

| Gly | Gly | Phe | Met | Pro | Phe | Gly | Phe | Ser | Gly | Val | Leu | Ser | Gly | Ala | Ala | Thr |
|---|---|---|---|---|---|---|---|---|---|---|---|---|---|---|---|---|
| 35 | | | | | 40 | | | | | 45 | | | | | 50 | |

| Cys | Phe | Tyr | Ala | Phe | Val | Gly | Phe | Asp | Cys | Ile | Ala | Thr | Thr | Gly | Glu | Glu |
|---|---|---|---|---|---|---|---|---|---|---|---|---|---|---|---|---|
| | | | 55 | | | | | 60 | | | | | 65 | | | |

```
Val  Lys  Asn  Pro  Gln  Lys  Ala  Ile  Pro  Val  Gly  Ile  Val  Ala  Ser  Leu  Leu
     70             75                       80                       85

Ile  Cys  Phe  Ile  Ala  Tyr  Phe  Gly  Val  Ser  Ala  Ala  Leu  Thr  Leu  Met  Met
               90                  95                       100

Pro  Tyr  Phe  Cys  Leu  Asp  Ile  Asp  Ser  Pro  Leu  Pro  Gly  Ala  Phe  Lys  Asn
          105                 110                      115

Gln  Gly  Trp  Glu  Glu  Ala  Lys  Tyr  Ala  Val  Ala  Ile  Gly  Ser  Leu  Cys  Ala
120                      125                 130                           135

Leu  Ser  Thr  Ser  Leu  Leu  Gly  Ser  Met  Phe  Pro  Met  Pro  Arg  Val  Ile  Tyr
               140                      145                 150

Ala  Met  Ala  Gln  Asp  Gly  Leu  Leu  Phe  Lys  Phe  Leu  Ala  Lys  Ile  Asn  Asn
     155                      160                      165                      170

Arg  Thr  Lys  Thr  Pro  Val  Ile  Ala  Thr  Val  Thr  Ser  Gly  Ala  Ile  Ala  Ala
               175                      180                      185

Val  Met  Ala  Phe  Leu  Phe  Glu  Leu  Lys  Asp  Leu  Val  Asp  Leu  Met  Ser  Ile
          190                      195                 200

Gly  Thr  Leu  Leu  Ala  Tyr  Ser  Leu  Val  Ala  Ala  Cys  Val  Leu  Val  Leu  Arg
205                      210                 215                      220

Tyr  Gln  Pro  Glu  Gln  Pro  Asn  Leu  Val  Thr  Gln  Met  Ala  Arg  Thr  Thr  Glu
               225                 230                      235

Glu  Leu  Asp  Arg  Val  Asp  Gln  Asn  Glu  Leu  Val  Ser  Ala  Ser  Glu  Ser  Gln
     240                      245                 250                           255

Thr  Gly  Phe  Leu  Pro  Val  Ala  Glu  Lys  Phe  Ser  Leu  Lys  Ser  Ile  Leu  Ser
               260                      265                 270

Pro  Lys  Asn  Val  Glu  Pro  Ser  Lys  Phe  Ser  Gly  Leu  Ile  Val  Asn  Ile  Ser
          275                      280                 285

Ala  Gly  Leu  Leu  Ala  Ala  Leu  Ile  Ile  Thr  Val  Cys  Ile  Val  Ala  Val  Leu
290                      295                 300                      305

Gly  Arg  Glu  Ala  Leu  Ala  Glu  Gly  Thr  Leu  Trp  Ala  Val  Phe  Val  Met  Thr
               310                 315                 320

Gly  Ser  Val  Leu  Leu  Cys  Met  Leu  Val  Thr  Gly  Ile  Ile  Trp  Arg  Gln  Pro
325                      330                 335                           340

Glu  Ser  Lys  Thr  Lys  Leu  Ser  Phe  Lys  Val  Pro  Phe  Val  Pro  Val  Leu  Pro
               345                      350                 355

Val  Leu  Ser  Ile  Phe  Val  Asn  Ile  Tyr  Leu  Met  Met  Gln  Leu  Asp  Gln  Gly
          360                 365                 370

Thr  Trp  Val  Arg  Phe  Ala  Val  Trp  Met  Leu  Ile  Gly  Phe  Thr  Ile  Tyr  Phe
375                      380                 385                      390

Gly  Tyr  Gly  Ile  Trp  His  Ser  Glu  Glu  Ala  Ser  Leu  Ala  Ala  Gly  Gln  Ala
               395                 400                 405

Lys  Thr  Pro  Asp  Ser  Asn  Leu  Asp  Gln  Cys  Lys
410                      415                 419
```

( 2 ) INFORMATION FOR SEQ ID NO:5:

( i ) SEQUENCE CHARACTERISTICS:
        ( A ) LENGTH: 44
        ( B ) TYPE: amino acid
        ( C ) STRANDEDNESS: single
        ( D ) TOPOLOGY: linear ( i i ) MOLECULE TYPE:
        ( A ) DESCRIPTION: peptide ( i i i ) HYPOTHETICAL: No ( i v ) ANTI-SENSE: No ( v i ) ORIGINAL SOURCE:

(B) STRAIN:
(C) INDIVIDUAL ISOLATE:
(D) DEVELOPMENTAL STAGE:
(F) TISSUE TYPE:
(G) CELL TYPE:
(H) CELL LINE:

(xi) SEQUENCE DESCRIPTION: SEQ ID NO:5:

Gly Ser Met Phe Pro Met Pro Arg Val Ile Tyr Ala Met Ala Glu Asp Gly
                  5                   10                  15
Leu Leu Phe Lys Phe Leu Ala Lys Ile Asn Asn Arg Thr Lys Thr Pro Val
            20                  25                  30
Ile Ala Thr Val Thr Ser Gly Ala Ile Ala
35              40          44

(2) INFORMATION FOR SEQ ID NO:6:

(i) SEQUENCE CHARACTERISTICS:
  (A) LENGTH: 44
  (B) TYPE: amino acid
  (C) STRANDEDNESS: single
  (D) TOPOLOGY: linear (ii) MOLECULE TYPE:
  (A) DESCRIPTION: peptide (iii) HYPOTHETICAL: No (iv) ANTI-SENSE: No (vi) ORIGINAL SOURCE:
  (B) STRAIN:
  (C) INDIVIDUAL ISOLATE:
  (D) DEVELOPMENTAL STAGE:
  (F) TISSUE TYPE:
  (G) CELL TYPE:
  (H) CELL LINE:

(xi) SEQUENCE DESCRIPTION: SEQ ID NO:6:

Gly Ser Ile Phe Pro Met Pro Arg Val Ile Tyr Ala Met Ala Glu Asp Gly
                  5                   10                  15
Leu Leu Phe Lys Cys Leu Ala Gln Ile Asn Ser Lys Thr Lys Thr Pro Val
            20                  25                  30
Ile Ala Thr Leu Ser Ser Gly Ala Val Ala
35              40          44

(2) INFORMATION FOR SEQ ID NO:7:

(i) SEQUENCE CHARACTERISTICS:
  (A) LENGTH: 43
  (B) TYPE: amino acid
  (C) STRANDEDNESS: single
  (D) TOPOLOGY: linear (ii) MOLECULE TYPE:
  (A) DESCRIPTION: peptide (iii) HYPOTHETICAL: No (iv) ANTI-SENSE: No (vi) ORIGINAL SOURCE:
  (B) STRAIN:
  (C) INDIVIDUAL ISOLATE:
  (D) DEVELOPMENTAL STAGE:
  (F) TISSUE TYPE:
  (G) CELL TYPE:
  (H) CELL LINE:

(xi) SEQUENCE DESCRIPTION: SEQ ID NO:7:

Gly Ser Met Phe Pro Leu Pro Arg Ile Leu Phe Ala Met Ala Arg Asp Gly

```
                              5              10             15
Leu Leu Phe Arg Phe Leu Ala Arg Val Ser Lys Arg Gln Ser Pro Val Ala
                20                      25                  30
Ala Thr Met Thr Ala Gly Val Ile Ser
 35              40          43
```

(2) INFORMATION FOR SEQ ID NO:8:

(i) SEQUENCE CHARACTERISTICS:
        (A) LENGTH: 435 bases
        (B) TYPE:nucleic acid
        (C) STRANDEDNESS: double
        (D) TOPOLOGY:linear (ii) MOLECULE TYPE:
        (A) DESCRIPTION: cDNA (iii) HYPOTHETICAL: No (iv) ANTI-SENSE: No (vi) ORIGINAL SOURCE:
        (B) STRAIN:
        (C) INDIVIDUAL ISOLATE:
        (D) DEVELOPMENTAL STAGE:
        (F) TISSUE TYPE:
        (G) CELL TYPE:
        (H) CELL LINE:

(xi) SEQUENCE DESCRIPTION: SEQ ID NO:8:

```
CTGCCCTGCC  CACACGACAG  TCGGCTTCCC  TTGTGAGCTT  TCTGGTGGGA      50
TTCCTGGCTT  TGGAAGCCTG  GAGCCTGGCT  CTTCTCGCCC  TGTTCCTTGT     100
CCTCTGCGCT  GCCGTCATTC  TGACGTTTCT  GCCGGCCTTC  AGCATCCTGG     150
TCAACATTTA  CTTGATGGTC  CAGTTAAGTG  CGGACAGCAT  TAGACACAGC     200
TTGGAGGGTA  ACCCCAGGGA  CGAAGAAGAC  GATGAGGATG  CCTTTTCACC     250
AAAGAAACCT  CAGCTTACCT  TTCATACTTC  ATGAAAAGAC  AAGTGAATGT     300
TGATGCTGGC  ATCGTGCTGG  GCTGTCGTGG  GTCTGCTGTG  GACATGGCTT     350
GCCTAACTTG  TACTTCCTCC  TCTCCTCAGC  TATATGTATC  CCCAAAACAG     400
TATGTCCGTG  TGCGTACATG  TATGTCTGCG  ATGTG                      435
```

(2) INFORMATION FOR SEQ ID NO:9:

(i) SEQUENCE CHARACTERISTICS:
        (A) LENGTH: 435 bases
        (B) TYPE:nucleic acid
        (C) STRANDEDNESS: double
        (D) TOPOLOGY: linear (ii) MOLECULE TYPE:
        (A) DESCRIPTION: cDNA (iii) HYPOTHETICAL: No (iv) ANTI-SENSE: No (vi) ORIGINAL SOURCE:
        (B) STRAIN:
        (C) INDIVIDUAL ISOLATE:
        (D) DEVELOPMENTAL STAGE:
        (F) TISSUE TYPE:
        (G) CELL TYPE:
        (H) CELL LINE:

(xi) SEQUENCE DESCRIPTION: SEQ ID NO:9:

```
AGAACGTGGA  GCCCTCCAAA  TTCTCAGGGC  TAATTGTGAA  CATTTCAGCC      50
```

```
GGCCTCCTAG  CCGGGACACT  GTGGGCAGTC  TTTGTAATGA  CAGGGTCAGT          100

CCTCCTCTGC  ATGCTGGTGA  CAGGCACCGT  ACTTCCTGTC  TTGAGCATCT          150

TCGTGAACAT  CTATCTCATG  ATGCAGCTGG  ACCAGGGCAG  GATCTGGCAC          200

AGTGAGGAAG  CGTCCCTGGC  TGCTGGCCAG  GCAAAGACTC  CTGACAGCAA          250

CTGCCCGTAG  AAGCCTGGGA  CCCTCACAAT  CTCTCCACTC  ATGCCTCAGG          300

ATCAGCTCAC  AGACAGTCCC  TTGGTTTACT  CATCTCCCTC  TGAACAAAGA          350

AAGCAGCCCT  TCTCCTTGCC  GGCTCCTCTC  ACTTGGGAAG  CAGGCCTCCC          400

TCCCTCCCTG  GGACCACCCT  GGCATCGCCC  ATGTG                           435
```